(12) United States Patent
Rao

(10) Patent No.: US 6,673,532 B2
(45) Date of Patent: Jan. 6, 2004

(54) BIOREACTOR AND BIOPROCESSING TECHNIQUE

(75) Inventor: Govind Rao, Columbia, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 114 days.

(21) Appl. No.: 09/928,662

(22) Filed: Aug. 14, 2001

(65) Prior Publication Data

US 2002/0025547 A1 Feb. 28, 2002

Related U.S. Application Data

(60) Provisional application No. 60/225,108, filed on Aug. 14, 2000.

(51) Int. Cl.[7] .............................. C12Q 1/00; C12Q 1/68; C12M 1/34
(52) U.S. Cl. ........................... 435/4; 435/6; 435/287.1; 435/288.3; 435/288.7
(58) Field of Search ...................... 435/4, 287.1, 288.3, 435/288.7

(56) References Cited

U.S. PATENT DOCUMENTS

| | | | |
|---|---|---|---|
| 5,541,056 A | | 7/1996 | Huntley et al. |
| 5,614,378 A | * | 3/1997 | Yang et al. ..................... 435/41 |
| 5,624,537 A | * | 4/1997 | Turner et al. ............. 422/82.01 |
| 5,795,773 A | * | 8/1998 | Read et al. ............... 435/287.5 |

OTHER PUBLICATIONS

Chang et al., "Steam–Sterilizable, Fluorescence Lifetime–Based Sensing Film for Dissolved Carbon Dioxide", Biotechnol Prog, Mar.–Apr., 14 (2):326–331 (1998).
Bylund et al., "Influence of Scale–Up on the Quality of Recombinant Human Growth Hormone", Biotechnol Bioeng, 69:119–128 (2000).
Kostov et al., "Low–Cost Microbioreactor for High–Throughput Bioprocessing", Biotechnol Bioeng, Feb. 5, 72 (3):346–52 (2001).
S.B. Bambot et al., "Lifetime–based optical sensing of pH using resonance energy transfer in sol–gel films", Sensors and Actuators B 22 (1994) pp. 181–188.
Sipior et al., "A Lifetime–Based Optical CO2 Gas Sensor with Blue or Red Excitation and Stokes or Anti–Stokes Detection", Anal Biochem, May 20, 227 (2):309–18 (1995).
Gryczynski et al., "Polarization–Based Oxygen Sensor", Analyst, Jul., 124(7):1041–44 (1999).
Bambot et al., "Optical Oxygen Sensor Using Fluorescence Lifetime Measurement", Adv Ep Med Biol, 361:197–205 (1994).
Chae et al., "Framework for Online Optimization of Recombinant Protein Expression in High–Cell–Density *Escherichia coli* Cultures using GFP–Fusion Monitoring", Biotechnol Bioeng, Aug. 5, 69 (3):275–85 (2000).

DeLisa et al., "Monitoring GFP–Operon Fusion Protein Expression during High Cell Density Cultivation of *Excherichia coli* using an On–Line Optical Sensor", Biotechnol Bioeng, Oct. 5, 65(1) :54–64 (1999).
Isabelle Walther et al., "Performance of a miniaturized bioreactor in space flight: microtechnology at the service of space biology", Enz. Microb. Technol., vol. 27, pp. 778–783.
Gregor Liebsch et al., "Luminescence Lifetime Imaging of Oxygen, pH, and Carbon Dioxide Distribution Using Optical Sensors", Applied Spectroscopy vol. 54, pp. 548–559 (2000).
Yordan Kostov et al., "Low–cost device for ratiometric fluorescence measurements", Journal of the American Institute of Physics, pp. 4466–4470 (1999).
Y. Kostov et al., "Solid State Luminescence Phase–Shift Oxygen Sensor for Biotechnology", Chemical and Biochemical Engineering Quarterly, pp. 201–205 (1998).
Yordan Kostov et al., "Unique Oxygen Analyzer Combining a Dual Emission Probe and a Low–Cost Solid–State Ratiometric Fluorometer", Applied Spectroscopy, vol. 54, pp. 864–868 (2000).
Yordan Kostov et al., "All Solid–State GFP Sensor", Biotechnology and Bioengineering, vol. 70, No. 4, pp. 473–477 (Nov. 20, 2000).
Zhong Xu et al., "A novel fiber–optic pH sensor incorporating carboxy SNAFL–2 and Fluorescent wavelength–ratiometric detection", pp. 9–15.
Lisa Randers–Eichhorn et al., "On–Line Green Fluorescent Protein Sensor with LED Excitation", Biotechnology and Bioengineering, vol. 55, No. 6, pp. 921–926 (Sep. 20, 1997).
Shabbir B. Bambot et al., "Phase Fluorometric Sterilizable Optical Oxygen Sensor", Biotechnology and Bioengineering, vol. 43, pp. 1139–1145 (1994).

* cited by examiner

*Primary Examiner*—Jon P. Weber
*Assistant Examiner*—Kailash C. Srivastava
(74) *Attorney, Agent, or Firm*—Fleshner & Kim LLP

(57) ABSTRACT

The inventive bioprocessing system (and technique) relies on non-invasive optical chemical sensing technology wherein an optical excitation source excites an optical chemical sensor. The optical chemical sensor then emits luminescence or absorbs light which is measured by a detector. The luminescence emitted from the chemical sensor or the amount of light absorbed by the chemical sensor is related to the concentration of an analyte, such as oxygen. If the luminescence emitted changes, or if the amount of light absorbed changes, then the concentration of the analyte has changed. Using such a system to measure and adjust multiple parameters at one time allows one to efficiently and cost-effectively determine optimal conditions for a given cell type and/or cell environment, for example. By combining cell cultivation with optical chemical sensing technology, cultivation can be successfully and rapidly performed, controlled and monitored in small volumes in an automated, parallel fashion at less expense than current bioprocess techniques.

20 Claims, 14 Drawing Sheets

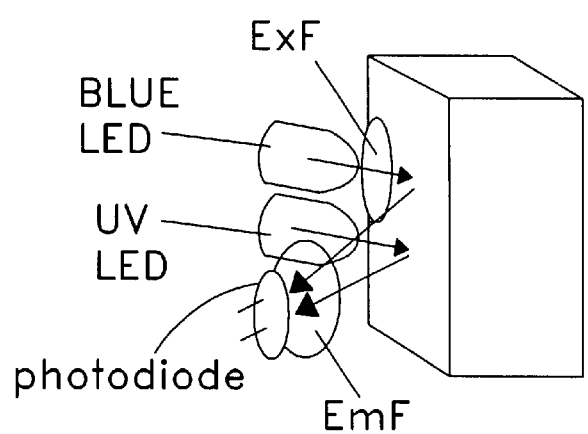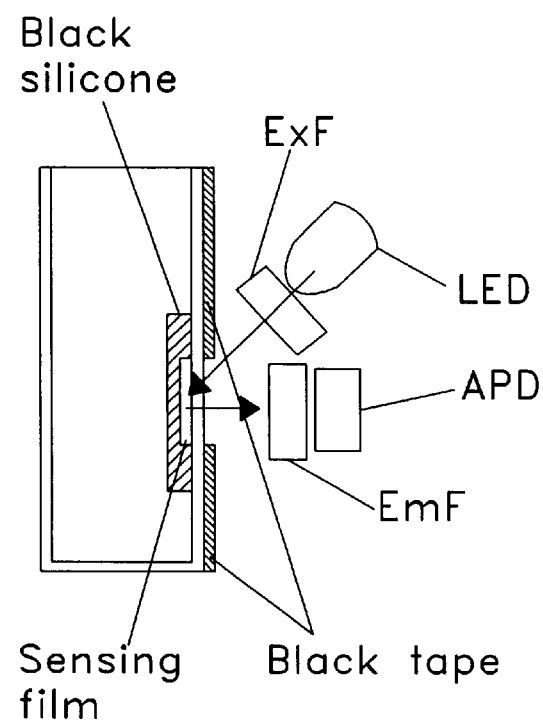
FIG. 3a                    FIG. 3b

BIOREACTOR AND BIOPROCESSING TECHNIQUE

This application claims priority to U.S. Provisional Application Ser. No. 60/225,108, filed Aug. 14, 2000, whose entire disclosure is incorporated herein by reference.

BACKGROUND OF THE INVENTION

1. Field of the Invention

The present invention pertains to a bioreactor, more particularly, a low volume bioreactor (microbioreactor). Further, the present invention pertains to the use of noninvasive optical chemical sensors to measure multiple parameters in a bioprocessing system.

2. Background of Related Art

Bioprocesses are important in a wide variety of industries such as pharmaceutical, food, ecology and water treatment, as well as to ventures such as the human genome project (Arroyo, M. et al., *Biotechnol. Prog.* 16: 368–371 (2000); Bakoyianis, V. and Koutinas, A. A., *Biotechnol. Bioeng.* 49: 197–203 (1996); Bylund, F. et al., *Biotechnol. Bioeng.* 69: 119–128 (2000); Handa-Corrigan, A. et al., *J. Chem. Technol. Biotechnol.* 71: 51–56 (1998); López-López, A. et al., *Biotechnol. Bioeng.* 63: 79–86 (1999); McIntyre, J. J. et al., *Biotechnol. Bioeng.* 62:576–582 (1999); Pressman, J. G. et al., *Biotechnol. Bioeng.* 62: 681–692 (1999); Yang, J.-D. et al., *Biotechnol. Bioeng.* 69: 74–82 (2000)).

The sequencing of the human genome has been a mammoth task, however, many have pointed out that this effort pales in comparison to what lies ahead. The next step is to identify what turns the identified genes on and what proteins these genes express. Cell cultivation will play a critical role in elucidating these factors. More specifically, after the 50,000–100,000 human genes are cloned into various hosts, such as bacteria, yeast and tissue culture cells, an enormous permutation of culture conditions will have to be evaluated to identify the critical factors that turn the genes on. Next, the identity of the proteins produced will have to be determined, thus, efficient production strategies will be needed to obtain enough proteins for crystallographic studies. A highly combinatorial technique could significantly speed up this identification process. Clearly, the ability to culture cells in controlled environments is crucial to this venture so that the benefits of human genome sequencing can be realized.

The ability to control the environment is also important in the area of new drug validation. Bioprocesses associated with new drugs are permitted a window of operating parameters, e.g., temperature, pH, etc., that are based on data obtained during the FDA approval process, wherein it has been demonstrated that the new drug is unaltered within that operating window. During production of the new drug, any deviation from the operating window results in the discarding of that batch of drug. Thus, a technique that permits more data to be generated by conducting experiments with wider parameter variation and thus, a wider operating window, could be a significant economic benefit to companies which currently have to discard batches of drugs.

Currently, for bioprocess development and optimization in the pharmaceutical industry, significant numbers of fermentations are needed under varying environmental and nutritional conditions. This is expensive and time-consuming in practice, as this type of research is typically performed in shake flasks (with practically no control of the bioprocess parameters) or in 1- to 100-liter laboratory scale bioreactors (Tholudur, A. et al., *Biotechnol. Bioeng.* 66: 1–16 (1999)). To decrease the number of experiments required for optimization, mathematical modeling is used (Alvarez-Ramirez, J. et al., *J. Chem. Technol. Biotechnol.* 74: 78–84 (1999); Boon, M. A. et al., *Biotechnol. Bioeng.* 64: 558–567 (1999); Cooney, M. J. et al., *Biotechnol. Prog.* 15: 898–910 (1999); Tholudur A. et al., *Biotechnol. Bioeng.* 66: 1–16 (1999)). However, this approach also requires a significant number of fermentations for establishing process parameters. Further, currently available laboratory scale bioreactors are expensive and bulky, thus making bioprocess development and optimization inefficient as large numbers of simultaneous experiments cannot be conducted.

To overcome the bulky aspect of scale bioreactors, miniaturized bioreactors have been used (Walther, I. et al., *Enzyme and Microbial Technol.* 27: 778–783 (2000)). However, in small volumes, e.g., 1–2 ml or less, it is difficult, if not impossible, to use standard industrial probes for culture monitoring due to the probes' physical dimensions. Another problem is that standard Clark-type oxygen probes consume oxygen (Lee, Y. H. and Tsao, G. T., *Advances in Biochemical Engineering*, Ghose, T. K. et al. (eds.), Berlin, Springer-Verlag, p. 35 (1979); Bambot, S. B. et al., *Biotech. Bioeng.* 43: 1139–1145 (1994)). In small volumes, such probes compete with the cells for oxygen which distorts the results from the bioprocess. In addition, over time, drifts in calibration can occur (Bambot, S. B. et al., *Biotech. Bioeng.* 43: 1139–1145 (1994)). Miniaturized versions of standard industry probes are known (Liu, C. C. and Neuman, M. R., *Diabetes Care* 5: 275–277 (1982); Suzuki, H. et al., *Biosens. Bioelectron.* 6: 395–400 (1991); Zhong, L. et al., *Chin. J. Biotechnol.* 8: 57–65 (1992)). However, their use in bioprocessing is not economically feasible due to the sophisticated and expensive techniques required to manufacture the miniaturized probes. Thus, a fast, reliable and inexpensive bioprocessing system and technique, wherein experiments can be performed, optionally in parallel, in small or large volumes, with on-line measurement and control of multiple process parameters, is strongly desirable.

SUMMARY OF THE INVENTION

The present invention combines bioprocessing with optical chemical sensing technology to monitor, measure, control and/or adjust and thus, to optimize multiple bioprocess parameters in single and/or multiple bioreactors.

In one embodiment, the invention is directed to a method of monitoring, measuring, controlling and/or adjusting and thus, optimizing at least two cultivation parameters in a cell culture, comprising:

(a) establishing at least one cell culture in at least one bioreactor, wherein each bioreactor comprises at least two optical chemical sensors;

(b) exciting the optical chemical sensors to generate emission and/or light absorption;

(c) detecting the emission and/or absorption obtained in (b);

(d) analyzing the detected emission and/or absorption obtained in (c) to determine the status of the cultivation parameters.

In another embodiment, the invention is directed to a method of monitoring, measuring, controlling and/or adjusting and thus, optimizing at least two cultivation parameters in at least two cell cultures, comprising:

(a) establishing at least one cell culture in at least two bioreactors in parallel, wherein each bioreactor comprises at least two optical chemical sensors;

(b) exciting the optical chemical sensors to generate emission and/or light absorption;

(c) detecting the emission and/or absorption obtained in (b);

(d) analyzing the detected emission and/or absorption obtained in (c) to determine the status of the cultivation parameters.

In another embodiment, the invention is directed to a bioprocessing system, comprising:

(a) at least one bioreactor;

(b) at least two optical chemical sensors associated with each bioreactor, wherein the optical chemical sensors are located within each bioreactor;

(c) at least one excitation source corresponding to each optical chemical sensor; and (d) at least one detector.

An object of the invention is to solve at least the above problems and/or disadvantages and to provide at least the advantages described hereinafter.

Additional advantages, objects and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The accompanying drawings, which are incorporated in and form a part of the specification, illustrate exemplary embodiments of the present invention and, together with the description, serve to explain the principles of the invention. In the drawings:

FIGS. 3(a) and 3(b) are schematic diagrams illustrating (a) an optical configuration of a pH channel; and (b) an optical configuration of an oxygen sensing channel. LED-light emitting diode; APD-avalanche photodiode; ExF-excitation filter; EmF-emission filter.

DETAILED DESCRIPTION OF PREFERRED EMBODIMENTS

A key requirement for any bioprocess is the ability to measure and control process parameters. In addition, if one is culturing cells, another key requirement is the ability to supply chemicals such as nutrients, oxygen and pH correctors, to the culture. The present invention meets these requirements and overcomes the disadvantages of known bioprocessing techniques by using non-invasive optical chemical sensing technology (Bambot, S. B. et al., *Biotechnol. Bioeng.* 43: 1139–1145 (1994); Randers-Eichhorn, L. et al., *Biotechnol. Bioeng.* 55: 921–926 (1997); Xu, Z. et al., *J. Biomed. Mater. Res.* 39: 9–15 (1998)) to monitor, measure, control and/or adjust and thus, to optimize multiple bioprocess parameters in single and/or multiple bioreactors.

The inventive bioprocessing system and technique removes a major bottleneck in bioprocess development and allows for much speedier and efficient optimization of bioprocesses such as fermentation. In addition, it could dramatically improve microbial isolation and cultivation of new species, as an enormous number of experimental conditions could be tested on a massively parallel scale.

Bioprocessing System

The inventive bioprocessing system (and technique) relies on optical chemical sensing technology wherein an excitation source produces light which excites an optical chemical sensor to generate emission and/or cause absorption. The emission and/or absorption is measured by a detector. The luminescence emitted from the chemical sensor or the amount of light absorbed by the chemical sensor is related to the concentration of an analyte, such as oxygen. If the luminescence emitted changes, or if the amount of light absorbed changes, then the concentration of the analyte has changed.

Since optical chemical sensing technology is employed in the inventive bioprocessing system, the following components must be included in the system: a bioreactor, chemical sensor, excitation (or light) source and detector. These elements are described in detail below. To conduct parallel bioprocessing, the system must contain at least two bioreactors each containing at least one chemical sensor. To measure multiple parameters, at least two chemical sensors must be present in each bioreactor (single or multiple bioreactors).

Figure 9:
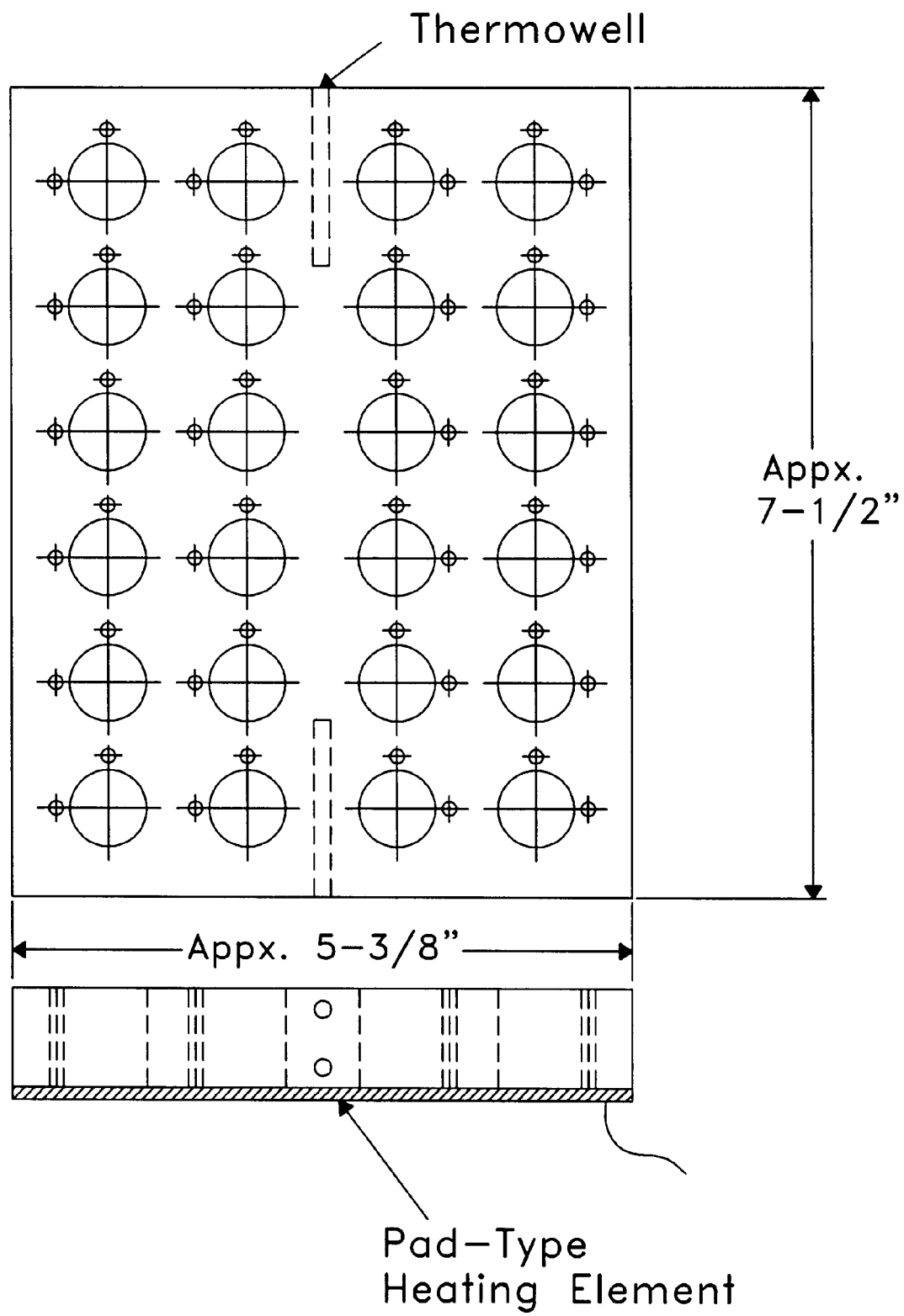
FIG. 9 is a schematic diagram of a bioreactor platform containing receptacles for 24 microbioreactors in accordance with one embodiment of the present invention wherein a pad-type heating element and thermowells are also present.
Figure 10:
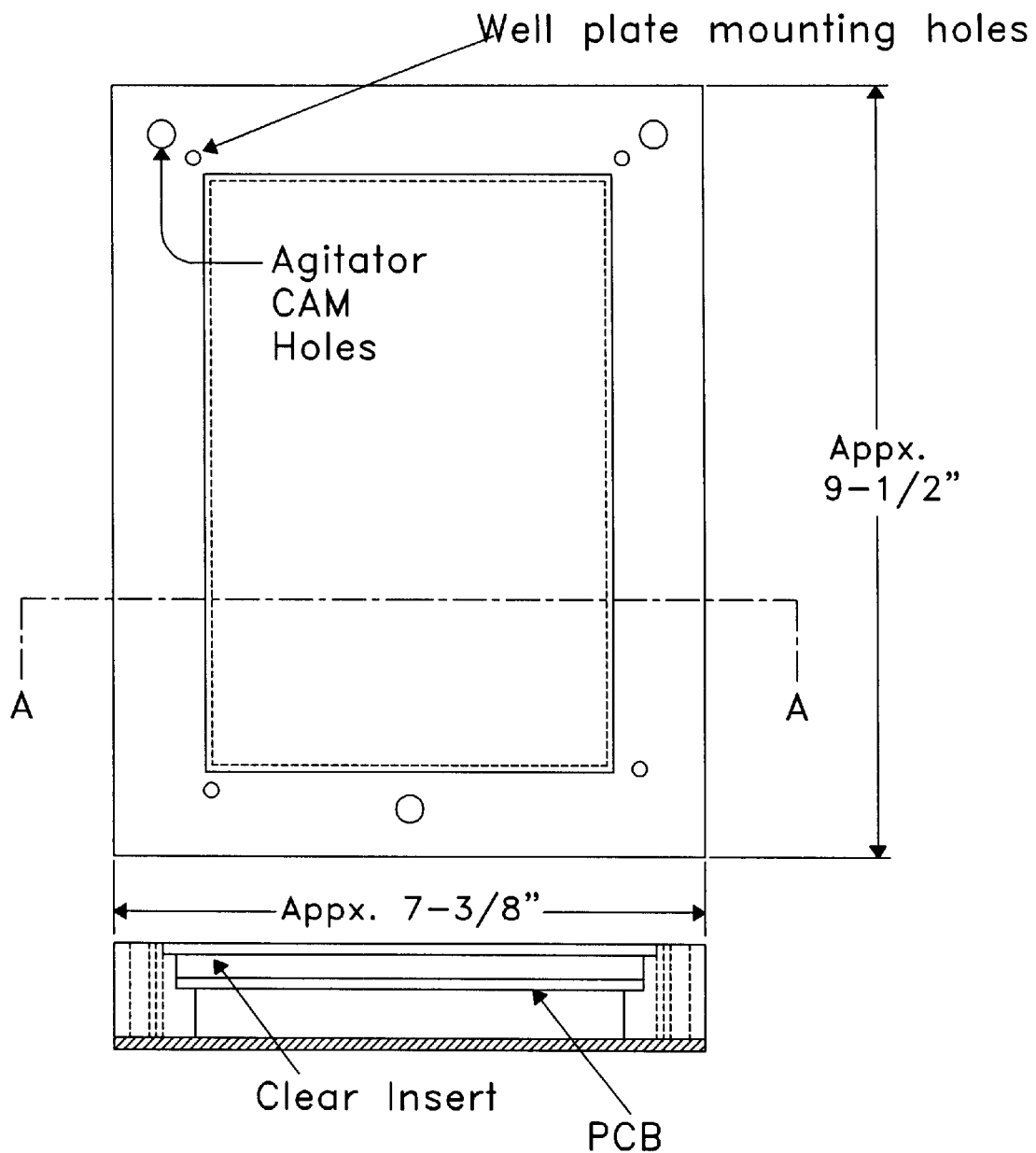
FIG. 10 is a schematic diagram of a sub-platform in accordance with one embodiment of the present invention wherein bioreactor platform and agitator mounting holes are present.

Optional components in the system are illustrated in FIGS. 7–12 and include the following:

Bioreactor Platform—the bioreactor platform, preferably a machined, anodized, aluminum plate, can function as a bioreactor holder. For example, the bioreactor platform could be used to hold culture vials (exemplary bioreactors) which cannot stand on their own. See, e.g., FIG. 7 and FIG. 9 (wherein the bioreactor platform has dimensions of about 7.5" by 5 and ⅜"). The bioreactor platform may be equipped with locator holes for light pipes and sparge tubes for each bioreactor. The locator holes keep the pipes and tubes fixed with respect to each bioreactor during agitation. In addition, the bioreactor platform can be equipped with thermowells to sense temperature. The bioreactor platform can be mounted to a sub-platform, described below, using mounting holes as illustrated in FIG. 10. If present, these two components function as a shaker mechanism for agitation control.

Figure 7:
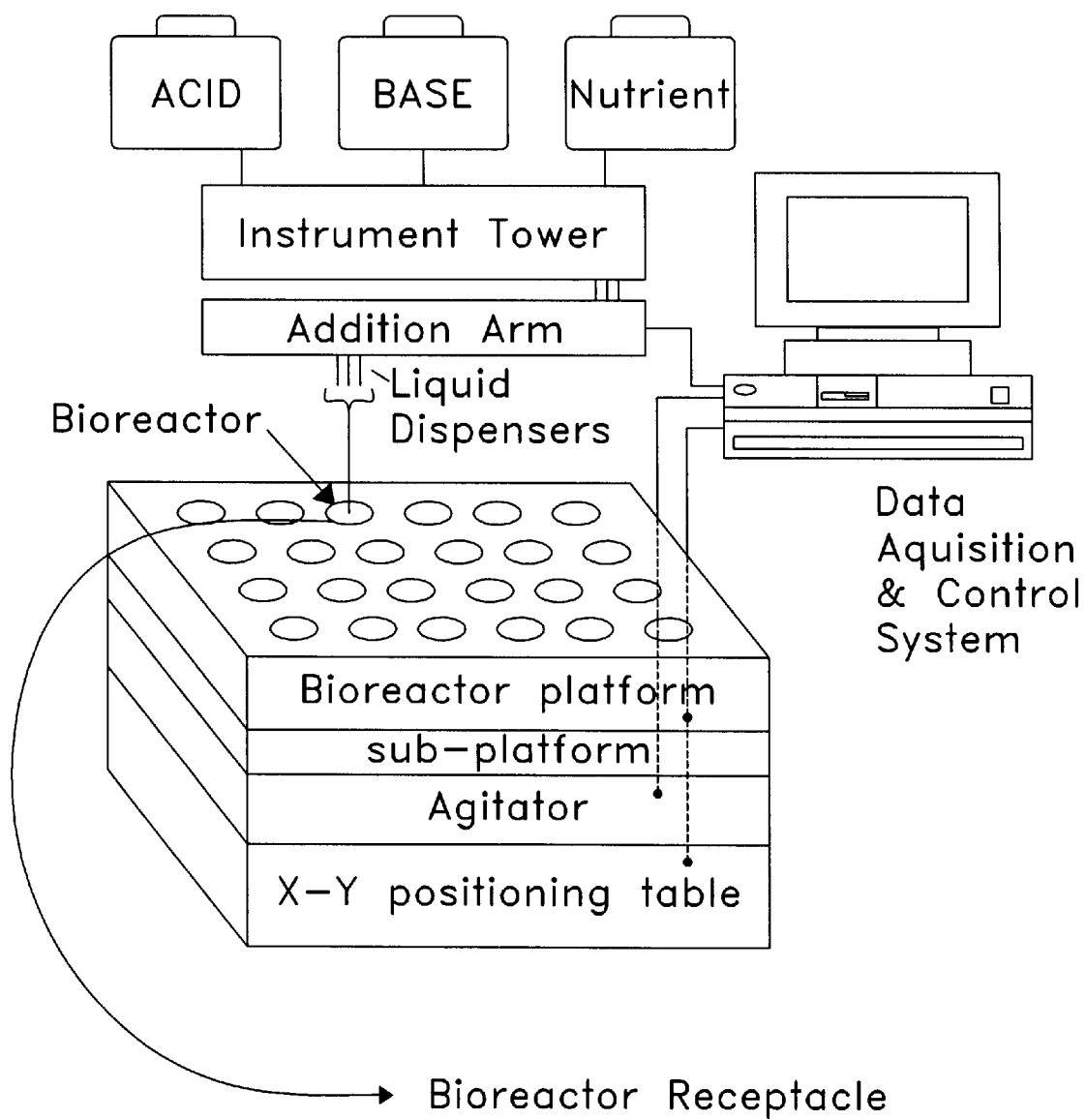
FIG. 7 is a schematic diagram of a microbioprocessing system in accordance with one embodiment of the present invention wherein acid, base and nutrient are added to the bioreactors through an instrument tower connected to a liquid addition arm connected to liquid addition tubes.

Sub-platform—the sub-platform houses the chemical sensors and any associated circuitry, such as signal conditioning and multiplexing components, wires harnessed to sensing electronics, etc., for each bioreactor. The sub-platform is preferably machined, made of aluminum and provided with an anodized finish. It can serve as a holder for the PCB (prototype circuit board) on which the optical components and electronics can be mounted. A clear, scratch-resistant insert can act as a stop for bioreactors such as culture vials, and as a window for the excitation sources and detectors. Alternate embodiments of a sub-platform are shown in FIG. 7 and FIG. 10 (wherein dimensions are indicated as about 9.5" by 7 and ⅜"). In a preferred embodiment, the sub-platform extends, on all sides, approximately one inch beyond the bioreactor platform, if present. This extension allows for mounting to an agitator for controlled agitation of the bioreactor platform/sub-platform assembly.

Cabling from the optical components and other electronic components (if such cabling is present), can be run in cable troughs to connectors mounted on one side of the sub-platform. From there, cabling (suitably strain-relieved) can run to the instrument housing, if present (described below).

Agitator—an agitator provides variable agitation, which is preferably selected using a software program, for example. See, e.g., FIG. 7. Agitation rate is preferably not uniform for each bioreactor. However, a uniform agitation rate can be readily employed. If a multi-well plate is used as a bioreactor, then it may be necessary to provide some means of agitating the plate so as to maintain sufficient dissolved oxygen levels within each bioreactor well. Alternatively, or additionally, dissolved oxygen levels can be maintained by sparging air at a fixed rate into the medium in each bioreactor.

Figure 11:
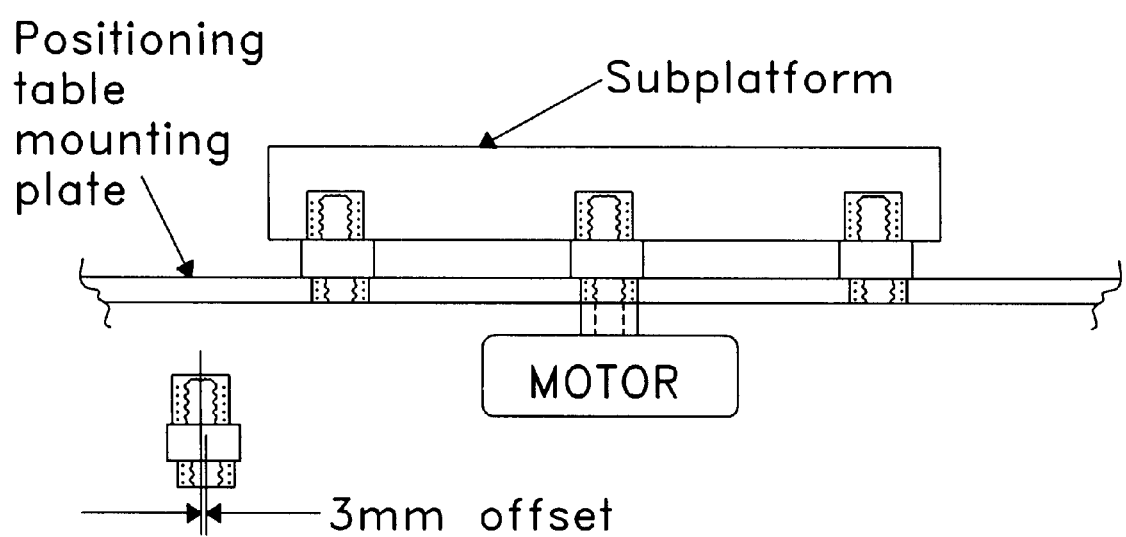
FIG. 11 is a schematic diagram of an agitator in accordance with one embodiment of the present invention wherein the agitator is connected to a sub-platform and mounting plate of a positioning table.

A variety of commercial agitators, such as shaker tables, are available, such as those manufactured by New Brunswick Scientific Co., Inc. and Innova LifeSciences Corp. However, commercial tables are usually designed for standalone operation with loads substantially higher than that expected from a bioreactor platform and sub-platform, for example, and they incorporate heavy cast-iron mechanisms designed to minimize travel when placed on a countertop or similar surface. In addition, because they are designed to work with large vessels, their orbital radii are generally greater than that which can be tolerated without resulting in splash-over from the bioreactor in the inventive system. For these reasons, a simple custom design can be employed in the inventive system incorporating a trio of small offset cams. See, e.g., FIGS. 10 and 11. One of these cams coupled to a variable speed DC motor is shown schematically in FIG. 11 connected to a mounting plate on a positioning table, described below. A 3 mm offset is indicated in FIG. 11. The motor minimizes overall height while providing orbital rates up to about 400 rpm.

The DC motor can be controlled by a commercially available motor control such as that manufactured by Dart Controls, Inc. The setpoint of the controller (displayed on a computer screen as 0–100% full scale) can be established by a computer based on manual operator entry or can be set automatically based on DO or $K_1a$. The 100% endpoint can be fixed to achieve a nominal orbital rate of about 350 rpm. Higher rates may create a funneling effect in the bioreactor which can skew DO measurements.

Alternatively, a simpler means of agitation, such as vibration, rocking, etc., could be employed. If vibrational agitation is selected, then control can be accomplished as described above for orbital agitation, except that the setpoint limits must be chosen to avoid splashing (instead of funneling).

Figure 12:
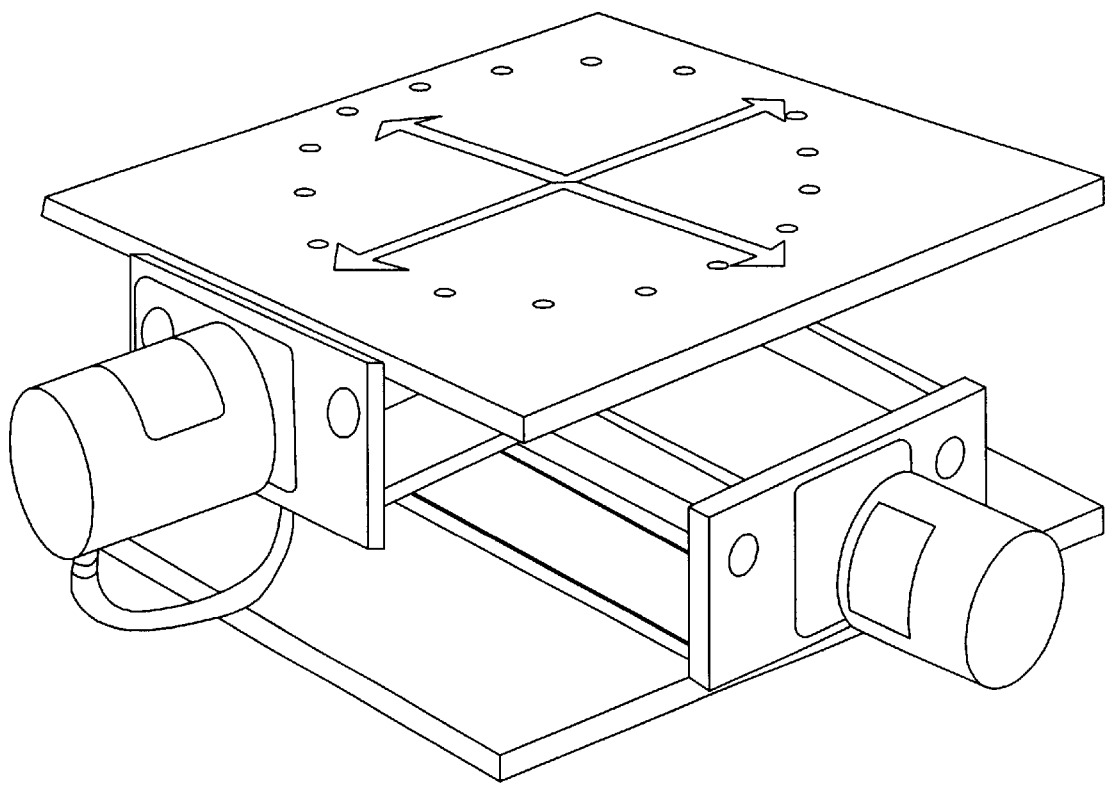
FIG. 12 is a photograph of a commercially available positioning table.

Positioning Table—a desirable positioning table has precise x-y axis control for the position of individual bioreactors, e.g., microtiter wells, under a robotic liquid addition arm, if present. See, e.g., FIG. 7. Although a number of x-y-z axis devices exist commercially (such as the DaVinci XYZ system by Techno-isel), they tend to provide more capabilities along the z-axis than is required for the inventive bioprocessing system. As a result, they tend to have a greater height than might otherwise be required and do not readily lend themselves to inclusion of an agitator. Therefore, an x-y axis device, such as the UniSlide® by Velmex, Inc. shown in FIG. 12, is preferred. By incorporating a pair of linear, low profile slides, suitable travel (such as 6"×9") can be achieved with minimum height (approximately 5.5") and foot print (approximately 23"×26" work envelope).

The positioning table may be provided with motors for positioning (rather than scanning) applications, e.g., with stepper motors and high precision lead screws. Outboard limit switches may also be provided. A custom top plate or mounting plate can be coupled via shock mounts to the shaker assembly, if present, to minimize vibrational transfer to the positioning table. Commercial controls, programmable as a Windows® application using an RS-232 port, for example, are available and may be utilized as a subcomponent of the positioning table. Alternatively, custom control, using an analog or digital position indication system with stepper motor controls, may be used.

Figure 1:
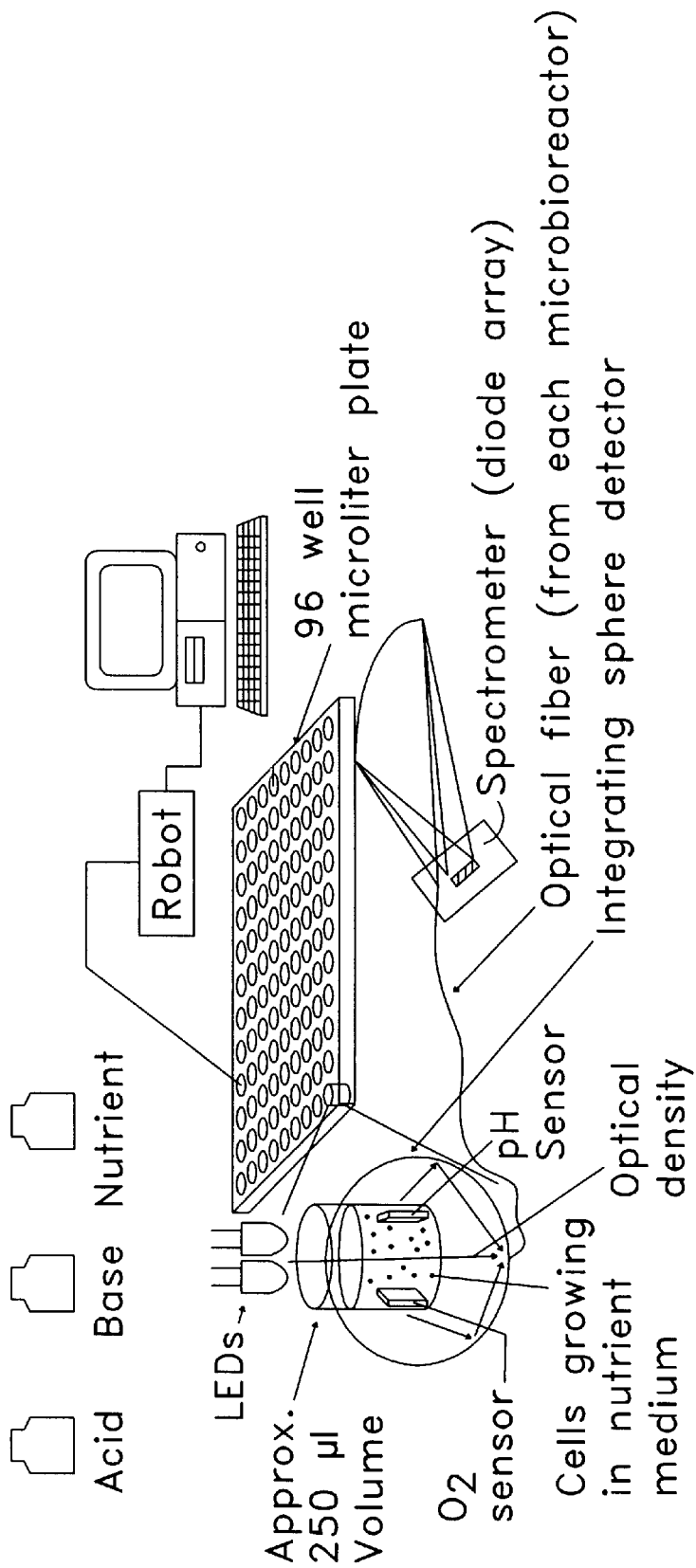
FIG. 1 is a schematic diagram of a high throughput microbioprocessing system in accordance with one embodiment of the present invention. In this embodiment, each well of a 96-well microtiter plate can be independently monitored for OD (optical density), pH and DO (dissolved oxygen) and independently controlled for pH and DO.
Figure 6:
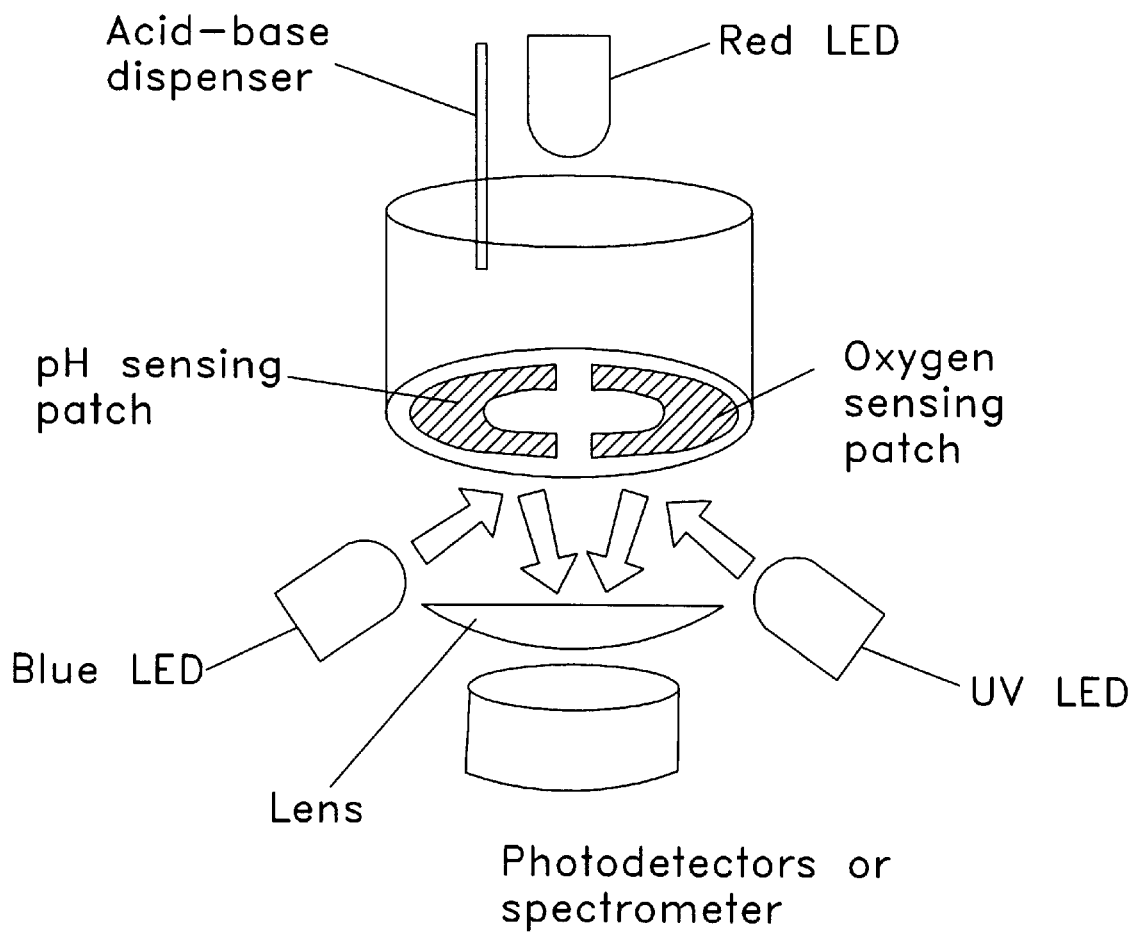
FIG. 6 is a schematic diagram of a single well of a multi-well plate illustrating an arrangement of optical elements and a pH reagent dispenser in accordance with one embodiment of the present invention. This particular arrangement permits movement of the plate in the x-y plane to enable each well to be monitored and to control pH.

Liquid Addition Arm—the liquid addition arm can be used to add chemicals, such as acid, base, nutrient(s), etc., to the bioreactors, as illustrated in FIGS. 1, 6 and 7. The liquid addition arm may be capable of z-axis motion to allow liquid dispensers to be positioned precisely above any given bioreactor, e.g., microtiter well. Thus, the chemicals can be dispensed into the culture medium, for example, to achieve more precise volume control and to avoid drop formation problems. A dual element syringe pump can be used to dispense the requisite chemical(s) to the bioreactors. The pump is a commercial device which can operate under computer control, and which can be housed in the instrument housing, if present. Alternatively, commercial micropipetters can be used, however, such devices add to the overall system height, which is a major consideration for a system designed to operate under a hood. In addition, the liquid addition arm may serve a second purpose—positioning a probe for pH measurements if the skilled artisan does not use optical pH sensors as described below. Thus, in addition to incorporating the outputs from the pump, if present, the liquid addition arm could also house a pH probe, if required. The liquid addition arm itself can be fixed to the x-y positioning table base plate, if present. A constant speed drive with limit switch and precision lead screw, or "pull"-type solenoid with spring return, can be used to provide the means of arm travel.

Air Manifold—the air manifold allows for the control of air (at an operator selected flow rate) to sparge elements in each bioreactor. See, e.g., FIG. 8. Flow rates to each bioreactor are preferably identical. Flow rate to the manifold can be manually set by the operator using, for example, a needle valve and flowmeter or a similar mechanism. Selecting and establishing flow rates are well-within the purview of the skilled artisan. Manifold inlet air supply may be filtered using a membrane filter such as an ACRO 50 0.2 $\mu$m PTFE filter.

Instrument Housing—the instrument housing contains liquid addition pumps, air system components, sensing electronics, motor drives, positioning controls, etc., if present. The housing can be interfaced to both the bioreactor platform, if present, and the control and acquisition computer (described below), if present. The housing is preferably a NEMA rated enclosure affixed to a base plate.

Computer-based Data Acquisition and Control System—the data acquisition and control system is, preferably, a computer-based system using data acquisition and control cards, manufactured by Measurement Computing Corp. of Massachusetts, for example. See, e.g., FIGS. 1 and 7. Such cards can be plug and play and auto-calibrating, without switches or jumpers, to facilitate replacement in the event of board failure.

Analog input channels in the data acquisition and control system preferably have 12-bit resolution with sampling rates up to about 330 kHz. Analog inputs can be software selected to function as single-ended or differential inputs, and input channel ranges can be software selectable as bipolar or unipolar from about 1.25 to about 10 V. Sampling in burst mode can be provided to minimize channel-to-channel skew by clocking the A/D at the maximum rate between successive channels. Signal conditioning can be provided for temperature inputs with a nominal half degree Celsius accuracy.

Analog outputs for use with external controllers, agitator motors, positioning tables, etc., if present, are preferably 12-bit and have discrete software selectable ranges.

Parallel digital I/O can be software selectable as input or output at byte or half-byte levels. Installation, calibration and testing software can be provided by the vendor for system management and testing.

Regarding software, commercially available software can be employed such as data acquisition cards, as described above, and graphical programs including, but not limited to, SoftWIRE®, LabVIEW®, etc. SoftWIRE® is a Visual Basic® based graphical programming language offered by Measurement Computing Corp. SoftWIRE® is menu-driven, highly intuitive and self-documenting. The software utilizes high-level control and graphical user interface (GUI) blocks that are compatible with all of Measurement Computing Corp.'s data acquisition and control cards. Because it is a Visual Basic® extension, it is readily interfaced to any other custom Visual Basic® application that might be required.

LabVIEW® is a software/hardware system that provides exceptional flexibility and one that has been used to control fermentations at the 1-liter and above scale. In addition, LabVIEW® provides mathematical operations that enable functions such as on-line growth and oxygen uptake rate calculations from real-time OD and DO data, if present.

The control, acquisition and GUI should be designed for a high degree of automation as well as system flexibility. In addition to performing the required control functions, it should permit: operator entry of system configuration data such as acid and base concentrations; operator configuration of bioreactors (individually or in blocks) including the ability to disable bioreactors as needed; control of the liquid addition arm, if present; control of the positioning table positions and movements, if present; operator entry of setpoints and control parameters; means of storing and retrieving previously stored configurations; operator selection of scan rates for DO levels, pH, etc.; logging of data to a disk after each measurement cycle or after multiple measurement cycles as specified by the operator; graphing of data as selected by operator from a variety of formats; alarming of abnormal conditions as per operator selection; and executing auxiliary functions such as calibration, homing, manual pump selection, etc. Thus, the data acquisition and control system can be used to monitor and control the bioreactors and to log parameters, including, but not limited to, temperature and agitation rates, for each bioreactor and/or the bioprocessing system as a whole.

Bioprocessing and Cell Cultivation

Monitoring, measuring, controlling and/or adjusting multiple parameters at one time allows the skilled artisan to efficiently and cost-effectively determine optimal conditions for a given cell type and/or cell environment. By combining cell cultivation with optical chemical sensing technology, cultivation can be successfully and rapidly performed, controlled and monitored in small volumes in an automated, parallel fashion at less expense than current bioprocess techniques. For example, a system wherein a plurality of bioprocesses, such as microbioprocesses, are conducted in a multi-well microtiter plate (as shown in FIG. 1), can be run for less than the cost of one benchtop bioreactor. Further, plate readers, found in nearly every cultivation laboratory, offer the opportunity for relatively inexpensive studies of the results of parallel bioprocesses (Li, J. et al., *Biotech. Bioeng.* 70: 187–196 (2000)). Thus, additional equipment may not be needed.

The bioreactor is preferably a cultivation vessel. It can be as large as a 1-, 3- or even 100-liter bioreactor or as small as a 100 $\mu$l well on a multi-well microtiter plate, or even as small as microchip, or anywhere in between. The size of the cultivation vessel will depend upon the experimental parameters, e.g., number of cell types, number of media, number of different conditions to test, etc. The skilled artisan can readily determine the appropriate cell cultivation vessel to employ. For example, if the skilled artisan has twelve different sets of conditions to determine growth optimization for a particular cell line, then a 12-well plate could be employed. Other cultivation vessel possibilities include, but are not limited to, cuvettes, culture plates such as 6-well plates, 24-well plates, 48-well plates and 96-well plates, culture dishes, microchips, 1-liter or larger bioreactors, cell culture flasks, roller bottles, culture tubes, culture vials, e.g., 3, 4 or 5 ml vials, flexible bags, etc. Thus, any type of container can be used as a cultivation vessel.

Depending upon their configuration within the well-plate, the wells on a well plate can function as microbioreactors or as receptacles, wherein a culture vessel such as a culture vial is placed in the receptacle and the culture vial becomes the bioreactor and the well plate becomes a bioreactor platform. Thus, in one embodiment, a bioprocessing system is employed wherein, for example, a machined, anodized, aluminum bioreactor platform contains receptacles for twenty-four 5 ml thick-walled, glass shell culture vials, as illustrated in FIG. 9. The culture vials are flat-bottomed vessels with a diameter and height of approximately 20 mm and each functions as a bioreactor. The vials are spaced on 35 mm centers.

Figure 2:
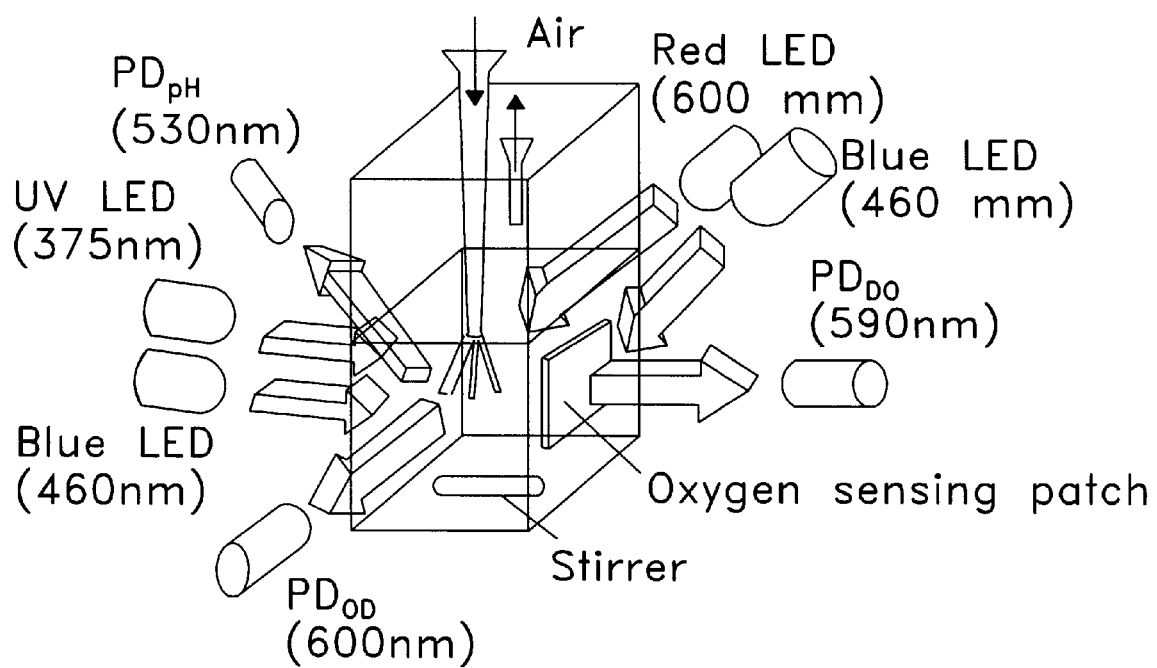
FIG. 2 is a schematic diagram of a microbioreactor in accordance with one embodiment of the present invention. In this embodiment, at the left cuvette wall, a blue LED (light emitting diode) and an UV LED, together with a 530 nm photodetector, are used to measure pH; at the right cuvette wall, a blue LED and a 590 nm photodetector are used to measure DO; a red LED and a 600 nm photodetector are used to measure OD through the front and back walls. The air supply inlet and outlet are positioned at the corners of the cuvette.

FIG. 2 illustrates another embodiment wherein a cuvette functions as a microbioreactor.

A single well from a multi-well plate, as seen in FIG. 6, is an example of another bioreactor, more specifically, a microbioreactor. A small operating volume of about 100 µl to about 250 µl is possible in such a bioreactor. See, e.g., FIG. 1 wherein each well in a 96-well microtiter plate functions as a microbioreactor containing approximately 250 µl cell-containing nutrient medium. Ideally, such a microbioreactor achieves a $K_1a$ approaching about 70 to about 100 $hr^{-1}$, which is comparable to a typical 1-liter laboratory fermentor run at about 700 to about 800 rpm at about 1 vvm (volume per volume per minute) aeration.

The cells undergoing cultivation are not limited to a particular cell type. In other words, the inventive bioreactor can be used to cultivate mammalian cells, insect cells, yeast, fungi, bacteria, protozoa, algae, plant cells, etc. Multiple cell types may be cultivated in parallel in different culture vessels or even in the same culture vessel, e.g., multi-well plate, so long as efforts are made to avoid cross-contamination.

The culture medium or media employed will depend upon the particular cell type(s) being cultivated. Determining the appropriate culture medium or media is well-within the purview of the skilled artisan. In the event that different culture media are being tested for optimization studies, then it would remain well-within the purview of the skilled artisan to determine which media to test based on the known basic nutrient requirements of the cell type(s). The $K_1a$ of the culture should be established to allow for cultivation without encountering oxygen limitations.

The culture parameters that can be monitored, measured and/or adjusted and thus, optimized, include, but are not limited to, pH, dissolved oxygen (DO), carbon dioxide level, temperature, glucose concentration, phosphate concentration, ammonia concentration, lactate concentration, metal ion(s) concentration(s), additional nutrient concentrations, flow rate, pressure, etc. Such parameters can be monitored continuously. Additionally, OD (optical density) can be monitored and measured.

Establishing controlled conditions is well-within the purview of the skilled artisan. For example, fermentations can be carried out in a humidified and temperature controlled oven placed in a sterile environment, such as a laminar flow hood to avoid contamination, or under similarly controlled conditions. Moreover, DO control can be carried out using a stirrer at the bottom of the bioreactor. See, e.g., FIG. 2. Alternatively, DO control can be carried out using an agitator that gently shakes, for example, an entire multi-well plate to allow for maximal oxygen mass transfer through the surface as described above. In a multi-well plate, the use of an agitator will cause all of the wells to have the same $K_1a$, thus allowing for meaningful comparisons to be made between experiments on a single plate. The agitation rate and the airflow rate combined determine a bioprocessing system $K_1a$. However, one could easily run multiple multi-well plates, for example, at different agitation settings to obtain a broad range of $K_1as$. Alternatively, individual wells of a multi-well plate, for example, can be independently agitated using a microelectromechanical system (MEMS) thereby permitting independent DO control of each well. The control and actuation can be implemented using LabVIEW®, for example, or similar system. DO control can be accomplished by controlling agitation rates and/or sparge flow rates to maintain desired average DO levels in a bioprocessing system containing multiple bioreactors, or, alternatively, to maintain minimum DO levels in single bioreactors. Software PID (proportional, integral, derivative) loops can be employed for this purpose.

pH control can be achieved by means of computer controlled addition of acid and/or base, i.e., pH correctors, to maintain pH around a chosen setpoint. In the present invention, precision syringe-pumps can be used to dispense quantities, including microliter quantities, of 1M HCl or NaOH as described above. A suitable degree of hysteresis may be necessary to prevent overcompensating through excessive liquid addition although the skilled artisan can have some flexibility in controlling the volumes of liquid that need to be added to adequately control pH.

Results from the continual monitoring can be employed as a feedback mechanism for adjusting the culture parameters. For example, feedback control of pH would be similar to that in lab fermentors wherein acid/base addition is initiated upon deviation from the setpoint.

Optical Chemical Sensing

There are five basic optical chemical sensing techniques: measuring absorbance, fluorescence intensity, ratiometric fluorescence, fluorescence lifetime and fluorescence polarization. Culture parameters such as pH and DO can be measured using any of the five techniques, however, the preferred technique is fluorescence lifetime. OD is measured via absorbance. Fluorescence lifetime is relatively immune to leaching, photobleaching, excitation light intensity and other artifacts which may affect fluorescence measurements. In fluorescence lifetime, a suitable quenching lumiphore is excited with modulated light and the lifetime (average time between absorption of a proton and the resultant fluorescence emission) is measured by determining the phase shift between the excitation light and the emission.

Excitation Source

As noted above, the excitation source produces light which excites the optical chemical sensor. The excitation source employed is preferably a light-emitting diode (LED) that emits light at a wavelength that corresponds to the excitation wavelength of the chemical sensor. For example, a blue LED and an UV LED are preferably used to measure pH when using a chemical sensor such as a 530 nm photodetector. A blue LED can also be used to measure DO when using a 590 nm photodetector. A red LED can be used to measure OD (a chemical sensor is not required to measure OD). If a multiple bioreactors are employed, then the skilled artisan could employ as many LEDs as there are bioreactors, as they are inexpensive. Alternatively, other excitation sources known in the art, e.g., laser diodes, can be used to illuminate the chemical sensor. A pass filter or excitation filter may be optionally positioned between each excitation source and its respective chemical sensor to block wavelengths other than those needed to excite the chemical sensor.

Detector

The detector employed to detect the luminescence emitted from or light absorbed by the optical chemical sensor can be a photodetector, spectrometer and/or diode array, photomultiplier tube (PMT), charge coupled device (CCD) camera, semiconductor photoreceiver or other detector known in the art. The design wavelength of the detector used is preferably matched to the luminescence wavelength of the respective chemical sensor. For example, if photodetectors are employed, then a 530 nm photodetector can be used to measure the luminescence from a pH chemical sensor, a 590 nm photodetector can be used to measure the luminescence from a DO chemical sensor and a 600 nm photodetector can be used to measure OD. A pass filter or emission filter may be optionally positioned between each chemical sensor and its respective detector to block wavelengths other than the luminescence wavelength of the chemical sensor.

Detection of bioprocess parameters can occur in numerous ways, depending upon the multiplexing of excitation sources and detectors. Multiplexing allows electronics to be shared by several chemical sensors. The combination of excitation sources and detectors will depend upon the system limitations, size of the bioreactor(s), cost and amount of space available.

For example, if the excitation source is an LED and if the detector can only detect emission over a limited wavelength range, e.g., a photodetector, then the following combinations could be employed:

provide at least one LED for each parameter being measured (via a respective chemical sensor) and provide at least one photodetector for each chemical sensor corresponding to the emission wavelength of the respective chemical sensor, wherein the LEDs and photodetectors move from bioreactor to bioreactor using a simple robot; or provide at least one LED for each parameter being measured (via a respective chemical sensor) for each bioreactor and provide, for each bioreactor, one photodetector for each chemical sensor corresponding to the emission wavelength of the respective chemical sensor.

If the excitation source is an LED and if the detector can analyze multiple wavelengths, then detection can occur via optical fibers coupled to a single diode array, for example. Specifically, one or more optical fibers can be used to couple the light emitted from the chemical sensors in each bioreactor to the diode array. For example, the fibers from each bioreactor in a multi-well plate can be brought to the detector and each bioreactor can be independently illuminated with an LED for the necessary excitation of the chemical sensor(s). This permits all the fibers to be coupled to the detector such that the data from each well is reported only when that well is illuminated. If necessary, an integrating sphere (a highly reflective surface, an example of which is shown in FIG. 1) can be positioned under each bioreactor to increase the light collection efficiency. Using this technique, each bioreactor can be read successively, as illustrated in FIG. 1. Thus, the following combinations could be employed:

provide at least one LED for each parameter being measured (via a respective chemical sensor), wherein the LEDs move from bioreactor to bioreactor using a simple robot, as illustrated in FIG. 1, or provide a wide area electroluminescent display for each parameter measured (via a respective chemical sensor), and provide one spectrometer for resolving the wavelengths of light emitted from the various chemical sensors; or provide at least one LED for each parameter being measured (via a respective chemical sensor) for each bioreactor and provide one spectrometer for each bioreactor.

An advantage of using a larger bioreactor, such as a cuvette, is that conventional optics employing photodetectors, for example, can be used which results in increased signal levels as substantially all the excitation light is coupled to the chemical sensors.

Figure 5:
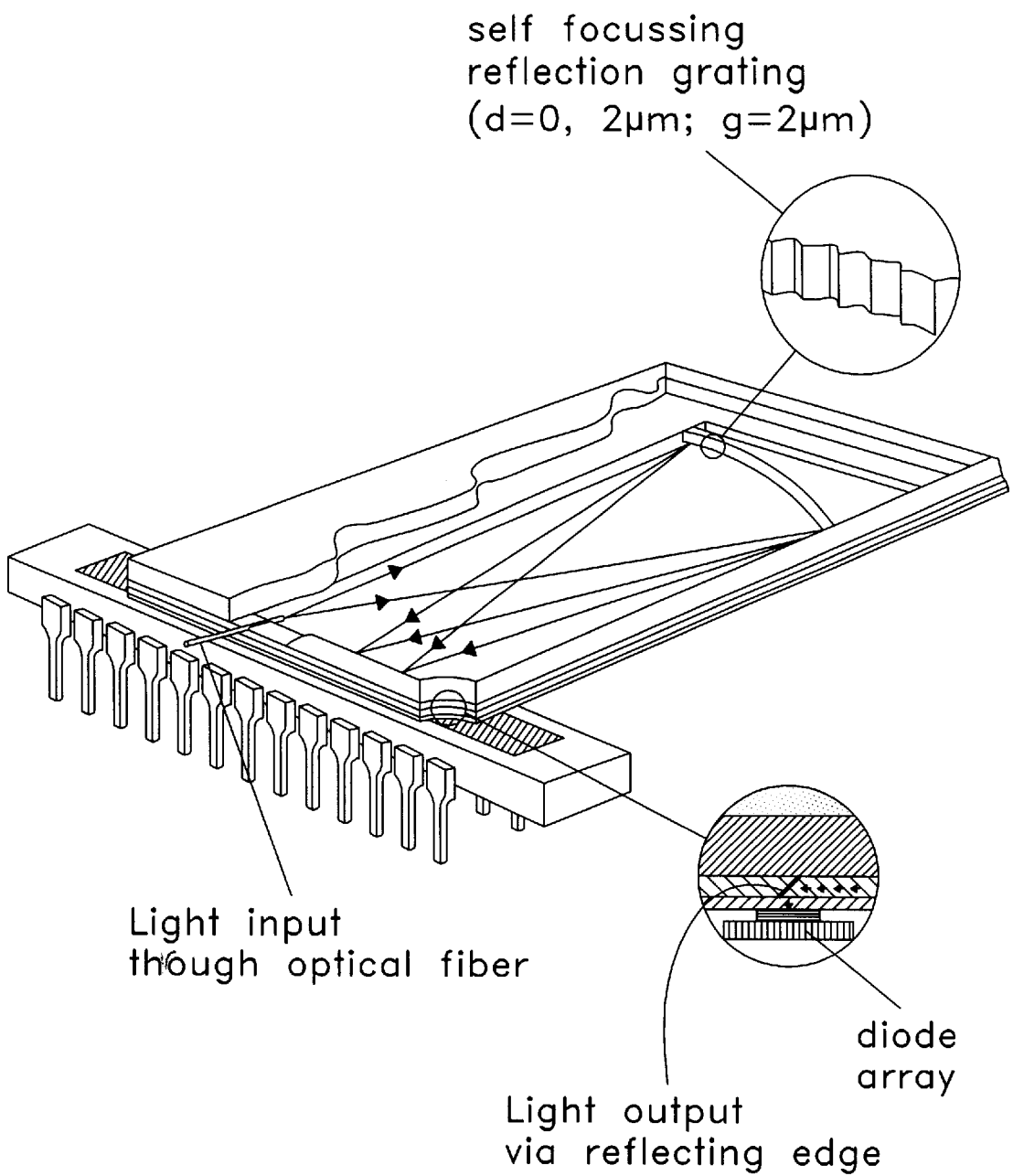
FIG. 5 illustrates a commercially available integrated spectrometer and diode array detector containing a self-focusing reflection grating (d=0.2 $\mu$m, g=2 $\mu$m), an optical fiber for light input, a reflecting edge for light output and a diode array.

An advantage of using a smaller bioreactor, such as a well on a microtiter plate, is that optical fibers can be used. When optical fibers are employed, an integrated spectrometer/detector capable of 2–3 nm resolution, for example, can be used. Such an integrated device is illustrated in FIG. 5, and is available from Microvision, Inc., Bothell, Wash. Use of this device eliminates the need for emission filters and thus, provides complete spectral information, which simplifies ratiometric measurements and provides additional flexibility in eliminating potential optical interferences.

Figure 8:
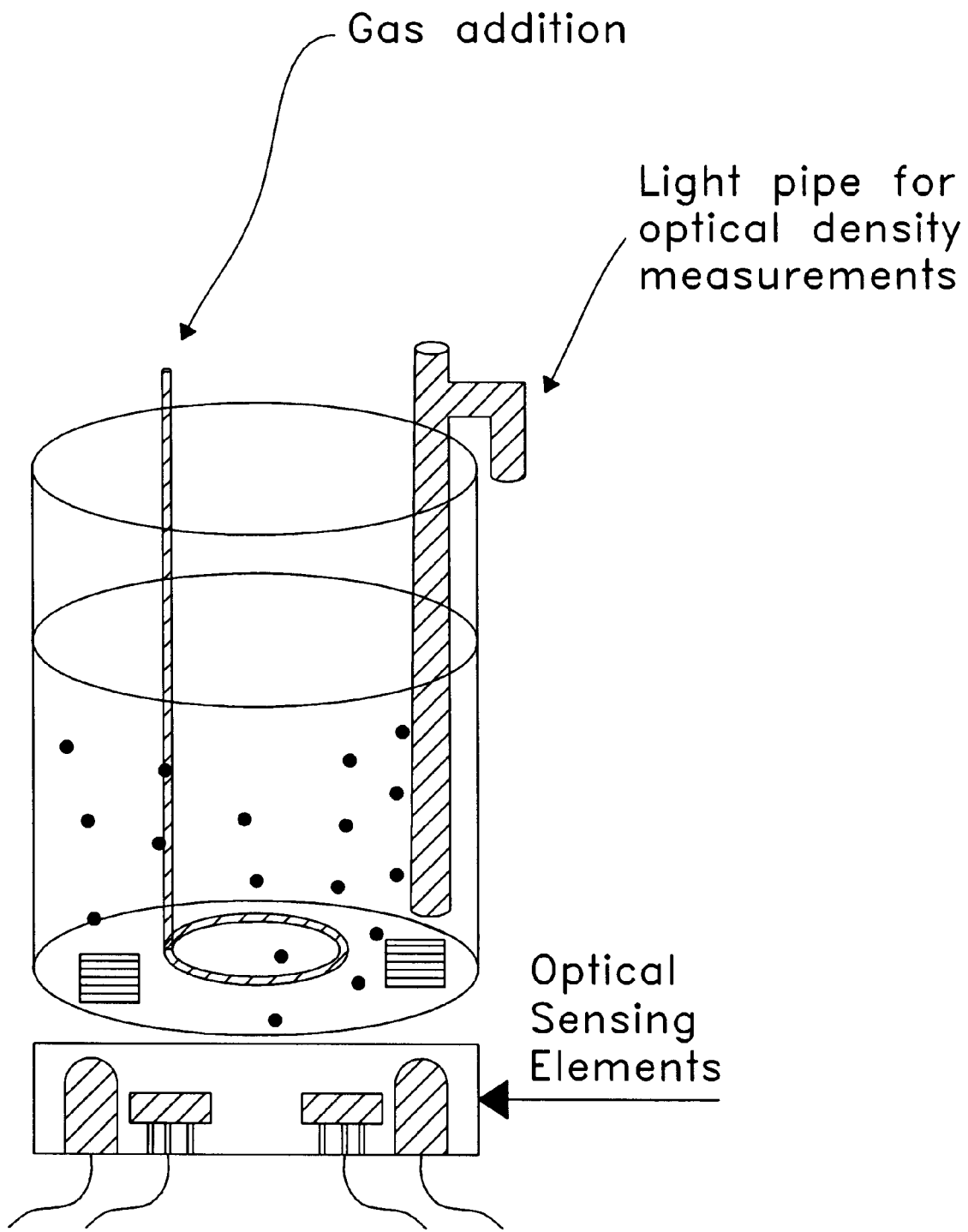
FIG. 8 is a schematic diagram of a microbioreactor in accordance with one embodiment of the present invention wherein the chemical sensors are located within the bioreactor and the chemical sensing electronics are located in a sub-platform. OD is measured via a light pipe and gas is added via a sparge tube.

Another embodiment is an arrangement wherein each bioreactor travels past a sensor head containing an LED and detector, positioned as illustrated in FIG. 2 for the single cuvette-based prototype. FIGS. 6 and 8 show possible arrangements of sensors for a single bioreactor in a multi-well plate. In FIG. 6, the pH and DO are read off the bottom of the well while the OD LED, e.g., red LED, rides along with the pH reagent dispenser above the well. The bottom of the well contains pH and oxygen sensor patches which are activated using blue and UV LEDs, respectively. A lens is used to maximize collected light emitted from the chemical sensors and direct it to the detector. In FIG. 8, DO and pH sensors are located in a sub-platform directly below the bottom of the well and OD is measured via a light pipe. These three arrangements would allow for the use of a positioning table, e.g., x-y platform, to move the multi-well plate.

Chemical Sensors

The number, types and sizes of optical chemical sensors employed can vary depending upon the chosen bioreactors. For example, the physical dimensions of the chemical sensors can be large for use with 1- to 100-liter bioreactors, or can be very small, e.g., optical fibers, for use with a microtiter well or microchip. Since optical chemical sensors are typically based on equilibrium principles, their presence in a cell culture will typically not interfere with cultivation. In other words, the chemical sensors are non-invasive.

Chemical sensors include, but are not limited to, fluorescent dyes added directly to the bioreactor medium, sensor "patches" applied to at least one wall of the bioreactor, sensing films applied to at least one wall of the bioreactor and any other optical chemical sensor known in the art. "Sensing films" and "sensor patches" are interchangeable phrases. The phrase "bioreactor walls" is intended to mean the sides, top and/or bottom of the bioreactor. Chemical sensor patches preferably comprise luminescent compounds immobilized in a polymeric membrane. Immobilization allows for maximum response, sensor reuse and minimal interference. If sensor patches are employed, they can be placed inside the bioreactor as illustrated in FIGS. 1, 2, 3(b) and 6, for example. Alternatively, as there is no need for physical contact with the detector, the chemical sensors can be sealed and sterilized.

The chemical sensor can be attached to the bioreactor wall using, for example, silicone grease. The grease prevents the chemical sensor from peeling off the wall and penetrating the medium between the sensor and the detector. As another alternative, the chemical sensor can be covered by a layer of black silicone for optical isolation from the fermentation medium, or the wall(s) of the bioreactor can be covered with black tape (with a window for exposing the chemical sensor to excitation light) to prevent excitation of the medium by the excitation light. These various alternatives can be practiced individually or in combination.

Since some of the components (especially the filters, if present) may be bigger than the bioreactor walls, e.g., cuvette walls, attention must be paid to the proper spatial placement of the optical components around the bioreactor to avoid optical crosstalk between the channels. Exemplary positioning of the basic components for pH and DO channels is shown in FIGS. 3(a) and 3(b), respectively.

pH

Chemical sensors used to measure pH include any known ratiometric pH sensitive dye, such as 1-hydroxypyrene-3,5, 7-sulfonic acid (HPTS). A sterilized solution of the dye can be directly introduced into the bioreactor medium and detected via fluorescence. Fluorescence detection can be determined using front face geometry (FIG. 3(a)). For example, HPTS has two excitation peaks—400 and 450 nm. When excited at either 400 or 450 nm, HPTS will emit light at approximately 520 nm. The longer excitation peak can be excited using a blue LED (460 nm), for example, and the shorter excitation peak can be excited using an UV LED (375 nm), for example. The intensity ratio of the 520 nm fluorescence emissions from excitation at each of the two excitation peaks is affected by the pH of the medium. Thus, the pH can be calibrated by measuring the intensity ratio of the 520 nm fluorescence emissions at each of the two excitation peaks as the pH changes. pH can be optionally verified on a benchtop pH meter. This ratiometric approach avoids interference from turbidity changes and provides accurate measurements of pH.

One possible problem with HPTS is the range of the emission spectrum since its emission maximum is 520 nm. To overcome this problem, the skilled artisan could employ green fluorescent protein (GFP). GFP is a pH sensitive dye which possesses a very similar emission spectrum to HPTS, but it emits at longer wavelengths. GFP can be used with an UV or a blue LED as the excitation source, depending upon background levels and the required sensitivity and selectivity (Kostov, Y. et al., *Biotechnol. Bioeng.* 70: 473–477 (2000)).

Another possibility is to measure pH using a nonradiative energy transfer system based on a sensing film wherein a ruthenium-based dye, for example ruthenium(II)-tris-(4,4'-diphenyl-2,2'-bipyridyl)-trimethylsilylpropansulfonate, functions as a luminescent donor, and a pH-sensitive dye, such as bromothylmolblue, functions as an acceptor. The sensing film is created by mixing the two dyes with a polymer, such as polyurethane, and applying it to a transparent support, such as polystyrene, using, for example, an ethanol-based solvent (Liebsch, G. I. et al., *Appl. Spectroscopy* 54: 548–559 (2000)).

Another possibility for measuring pH is to use an immobilized indicator dye. In fact, although it is not necessary, it is preferable for the indicator dye to be immobilized as long as it does not interfere with cell growth. Sol-gel chemistry and ethyl cellulose films have been successfully used to immobilize pH indicators (Bambot, S. B. et al., *Sensors and Actuators B* (*Chemical*) 22: 181–188 (1995); Chang, Q. et al., *Biotechnol. Prog.* 14: 326–331 (1998)). Epoxy resins may also work well as immobilization matrices.

A non-sensor based alternative can also be used if the bioreactor size is sufficient wherein a dip probe incorporating an ion selective FET (field effect transistor) is employed. Such a probe can be mounted on the end of the liquid addition arm, if present.

Oxygen

DO sensors include, but are not limited to, ruthenium-based oxygen sensing films such as Ru(II) tris (4,7-diphenyl-1,10-phenanthroline) complex, immobilized in a silicone rubber membrane (Bambot, S. B. et al., *Biotechnol. Bioeng.* 43: 1139–1145 (1994)). An exemplary optical configuration of the DO components is shown in FIG. 3(b) wherein black silicone film is attached to the bioreactor wall using silicone grease. In FIG. 3(b), a wall of the bioreactor is covered with black tape (with a window for the chemical sensor) to prevent excitation of the medium by the excitation source.

As an alternative, DO can be measured using a chemical sensor wherein an indicator dye such as a porphyrin dye, for example a metalloporphyrin such as platinum(II)-octaethylporphyrin, is combined with, e.g., encapsulated within, a polymer matrix such as polystyrene. The matrix layer is then applied to a polystyrene support using, for example a toluene-based solvent (Liebsch, G. I. et al., *Appl. Spectroscopy* 54: 548–559 (2000)).

As an alternative, ratiometric oxygen measurement based on a new class of compounds that show dual emission peaks, an oxygen insensitive and an oxygen sensitive one, can be employed. Such compounds include, but are not limited to, heterocyclic-substituted platinum 1,2-enedithiolates such as $BPh_4$ ((dppe)Pt{$S_2C_2(CH_2CH_2$—N-2-pyridinium)}, wherein "dppe" is 1,2-bis(diphenylphosphino)ethane) (Kostov, Y. et al., *Appl. Spectroscopy* 54. 864–868 (2000)). By measuring the ratio of the two emission peaks, the skilled artisan can quantify the ambient oxygen tension around the chemical sensor (Kostov, Y. and Rao, G., *Rev. Sci. Inst.* 70: 4466–4470 (1999)). An advantage of this technique is that it would allow the same circuitry to be employed for both DO and pH measurements. Another advantage of this technique is that it provides continuous calibration.

In all cases described above, DO is measured using luminescent quenching. Although, as noted above, dual emission compounds can be used in a ratiometric measurement system as well. In luminescent quenching, DO is detected using frequency domain detection of ruthenium or porphyrin fluorophore lifetime, for example, wherein the excitation light is modulated and the lifetime is measured by determining the phase shift between the modulated excitation light and the resulting modulated fluorescence emission. This is a well-established method of oxygen detection (Bambot, S. B. et al., *Biotechnol. Bioeng.* 43: 1139–1145 (1994)) and relies on the reversible quenching of fluorescence emission due to oxygen binding. Its greatest advantage is that the measurements are equilibrium based and do not consume oxygen.

DO calibration can be achieved using an air-nitrogen blending setup, for example, and recording the phase shift going from nitrogen to air. Thus, a simple calibration procedure will suffice, such as a single point calibration at 100% DO in a gas.

Temperature

Temperature can be measured using thermal deactivation techniques which employ, for example, dyes such as ruthenium-based dyes, for example ruthenium(II)-tris-(1,10-phenanthroline)-hexafluorophosphate, on a polymer matrix such as poly(acrylonitrile) using a di-methylformamide-containing solvent (Liebsch, G. I. et al., *Appl. Spectroscopy* 54: 548–559 (2000)). The polymer matrix prevents the quenching of the ruthenium complex by oxygen.

Alternatively, temperature can be measured using fluorescent probes that respond to temperature such that even individual bioreactor, e.g., well, temperature control can be obtained in a multi-well plate (Liebsch, G. I. et al., *Appl. Spectroscopy* 54: 548–559 (2000)) when the probes are combined with resistance-based heating.

Alternatively, temperature can be measured by thermistors or other sensing devices placed in thermowells, as illustrated in FIG. 9. Such devices can be wired through a data acquisition card to permit computer display, logging and control. Redundant readings can be averaged to determine the temperature.

If a bioprocessing system is employed wherein a bioreactor platform is present, then temperature can be measured and controlled via the bioreactor platform which can act as a heating element as it can be equipped with four thermowells for temperature sensing. See, e.g., FIGS. 7 and 9. For example, if the bioreactor is housed in a receptacle in a bioreactor platform, then a pad-type heating element, such as Chromalox® or its equivalent, can be sized so as to raise the top surface of the bioreactor platform from ambient temperature to a temperature of, for example, about 40 degrees C., within a period of, for example, about 15 to about 20 minutes. The pad-type heating element's power supply can be modulated in ON/OFF fashion by a computer controlled relay, so as to emulate a PID temperature controller. The pad-type heating element can be fabricated with holes to match those in the sub-platform, if present.

The bioreactor platform can be sized so that the combination of bioreactor platform and pad-type heating element has a thickness approximately equal to the height of each bioreactor. For example, if the bioreactors are culture vials, then the height of the bioreactor platform and pad-type heating element would be approximately equal to the culture vial height. If additional heating is needed for adequate temperature control, then the sub-platform, if present, can be fabricated as two layers with an additional heater between the layers. This decreases the temperature gradient across the bioreactor platform and allows for separately controlled "heating zones." If additional heating is needed, the overall height of the bioreactor system should still be equal to the height of the bioreactors.

Carbon Dioxide

Nonradiative energy transfer can be used to measure carbon dioxide levels. For example, indicator dye combinations such as a ruthenium-based dye, for example ruthenium (II)-tris-(4,4'-diphenyl-2,2'-bipyridyl)-trimethylsilylpropansulfonate and m-cresolpurple wherein the former is the donor and the latter is the acceptor, can function effectively to measure carbon dioxide presence (or absence) and changes thereof (Liebsch, G. I. et al., *Appl. Spectroscopy* 54: 548–559 (2000)). The two dyes can be added to an ethyl cellulose matrix using a toluene- and ethanol-containing solvent and then added to a polyester support.

Optical Density

The OD of the cell suspension in the medium can be directly measured using an LED that emits at approximately 600 nm, for example. Specifically, a yellow LED (595 nm) attached to each bioreactor's light pipe, if present, can be driven by a current source modulated at a predetermined frequency, thereby modulating the output light at the same predetermined frequency. The modulated light passes through the light guide, which is held in the medium a fixed distance from the bottom of the bioreactor, and is detected by a photodetector (which can be equipped with a 600 nm bandpass filter, if desired) mounted beneath the bottom of the bioreactor. Lock-in detection can be used to detect only light that is modulated at the predetermined frequency, thereby removing noise and the effects of ambient light (which is not modulated) from the signal. A calibration procedure for OD can be provided similar to that for DO, allowing the measurement of light at each photodetector prior to the addition of liquid to the associated bioreactor.

Alternatively, OD can be measured using conventional equipment such as a plate reader, or using microbore column chromatography or flow injection analysis.

Additional Applications

Apart from the obvious utility of allowing much speedier bioprocess development and optimization, the inventive bioprocessing system could open the way to discovering new species of microorganisms. The currently available strains are believed to be a small fraction of the total species. Since many microorganisms are thought to be simply uncultivable in a laboratory setting, an approach where an enormous number of culture conditions can be tried may target the optimal combination necessary for culturing novel microbes.

In addition, the inventive bioprocessing system is not limited to cell cultivation. For example, one skilled in the art could conduct enzymatic and other biological reactions in parallel to optimize conditions, determine parameters and/or conduct comparison studies. By interfacing with a fast analysis system such as capillary electrophoresis or perfusion chromatography, the inventive bioprocessing system could be automated even more such that product profiles are also available.

The invention is illustrated by the following example which is not intended to be limiting.

EXAMPLE 1

In this example, the working volume was scaled down to about 2 ml by using a disposable cuvette as the bioreactor. The design of the microbioreactor is presented in FIG. 2. Three parameters, pH, DO and OD, were continuously measured using optical chemical sensors. A test fermentation was performed in the microbioreactor and the results were compared with the results from a fermentation in a standard 1 liter bioreactor.

The working bioreactor was a disposable polystyrene cuvette, 1×1 cm, with a total volume of 4 ml. To avoid contamination during cultivation, it was equipped with a silicone rubber cap. The cap had an inlet for air delivery and outlet for exhaust air. The inlet and outlet were positioned at the corners of the cuvette to avoid overlapping with the optical path for OD measurements. The inlet was connected to an air sparger, as indicated in FIG. 2, which was fabricated from a 100 $\mu$l plastic pipette tip. Three tubes with inner diameters of 0.25 mm were positioned at the end of the tip. The tubes were glued using epoxy resin. The outlet consisted of a short piece of a 16-gauge syringe needle. The air was supplied by an aquarium pump, passed through a regulator for low gas flow rate and filtered using a syringe filter (Millex®-GV, 0.22 $\mu$m, Millipore, Bedford, Mass.). Stirring was executed by a small magnetic stir bar and magnetic stirrer. The $K_1a$ of the cuvette was adjusted to be approximately equal to the $K_1a$ of a 1-liter fermentor operated at 300 rpm agitation and 1 vvm aeration (21 $h^{-1}$).

The cuvette was large enough to accommodate conventional optics and electronics and thus, no optical fibers were needed. Solid state light sources, e.g., LEDs, and detectors, and low-cost optical filters and electronics were used. As some of the components (especially the filters) were bigger than the cuvette wall, attention was paid to the proper spatial placement of the optical components around the cuvette in order to avoid crosstalk between the channels. The positioning of the basic components for the pH and DO channels is shown in FIGS. 3(a) and 3(b), respectively.

The pH measurements were performed using the ratiometric pH sensitive dye 1-hydroxypyrene-3,5,7-sulfonic acid, (HPTS, Sigma, St. Louis, Mo.), pKa=7.2, a non-toxic indicator, used for blood gas measurements in vivo (Zhang, S. et al., *Med. Biol. Eng. Comput.* 33: 152–156 (1995)). The 7.2 pKa makes HPTS appropriate for use with neutral-range bioprocesses. A sterilized solution of HPTS was directly introduced into the culture media. Its addition to the media did not influence cell growth.

The absorbency of the cell suspension was directly measured using a 600 nm LED. For this particular setup, the maximum OD detected was approximately 9 (results not shown).

The DO channel was positioned on the opposite wall of the cuvette to the pH channel using the ruthenium-based oxygen sensor Ru(diphenylphenanthroline)$_3^{2+}$, immobilized in silicone rubber (Bambot, S. B. et al., *Biotechnol. Bioeng.* 43: 1139–1145 (1994)). The optical configuration of the components is shown in FIG. 3(b). The sensing film was attached to the cuvette wall using silicone grease (high vacuum grease, Dow Corning, Midland, Mich.). The sensing film was covered by a layer of black silicone (GE 312A, General Electric Company, Waterford, N.Y.) for optical isolation from the fermentation medium. The wall of the cuvette was covered with black tape (with a window for the chemical sensor) to prevent excitation of the medium.

Oxygen detection was performed using frequency domain detection of ruthenium fluorophore lifetime, wherein the excitation light was modulated and the lifetime was measured by determining the phase shift between excitation light and fluorescence emission (Bambot, S. B. et al., *Biotechnol. Bioeng.* 43: 1139–1145 (1994)). Calibration was achieved by using an air-nitrogen blending set-up and recording the phase shift going from nitrogen to air.

Figure 4A:
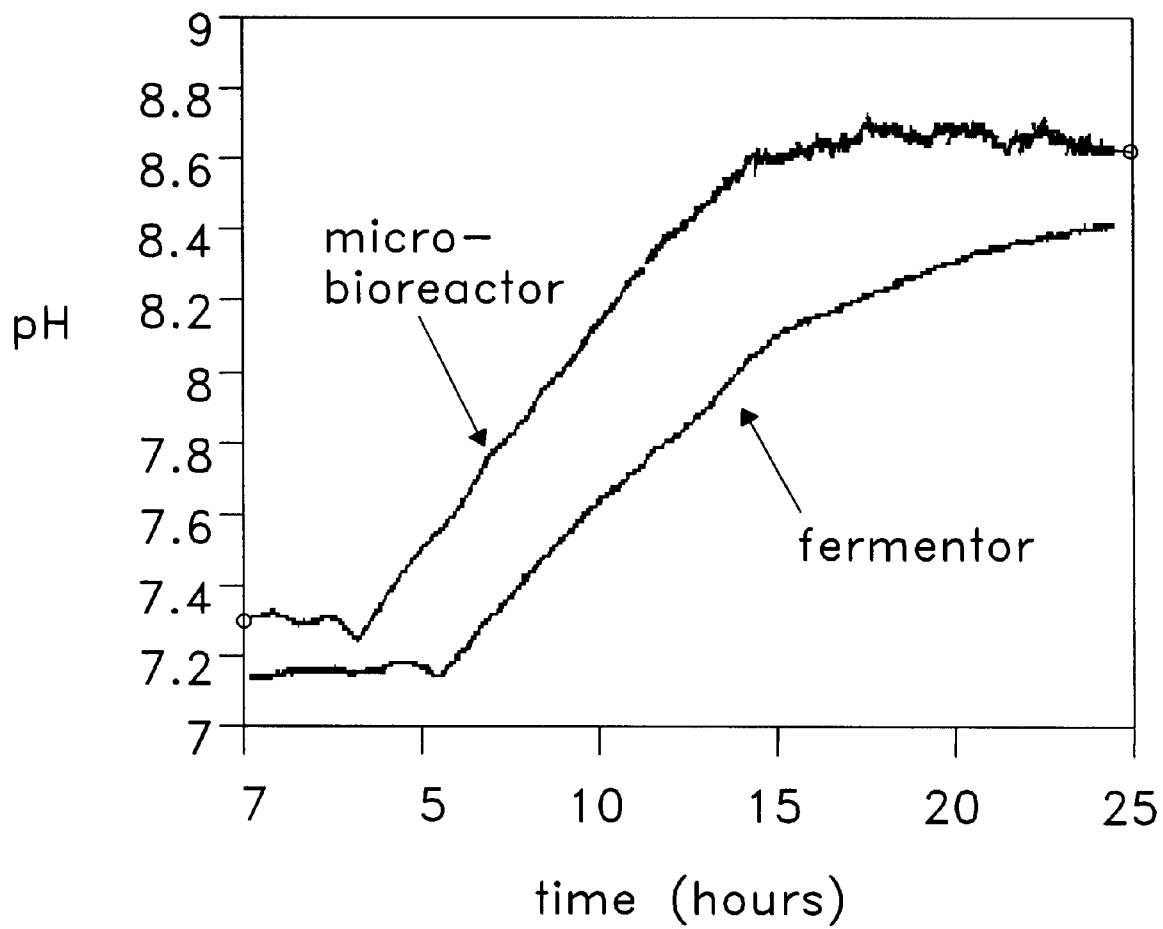
FIGS. 4(a)–4(c) are graphs illustrating three measured parameters during parallel fermentations of $E.\ coli$ in a microbioreactor and a 1-liter fermentor. Time profiles comparing (a) pH (the circles in the beginning and end represent the pH values measured with a standard pH meter); (b) DO; and (c) OD (the circles in the beginning and end represent the values measured with a spectrophotometer after dilution) are illustrated.
Figure 4B:
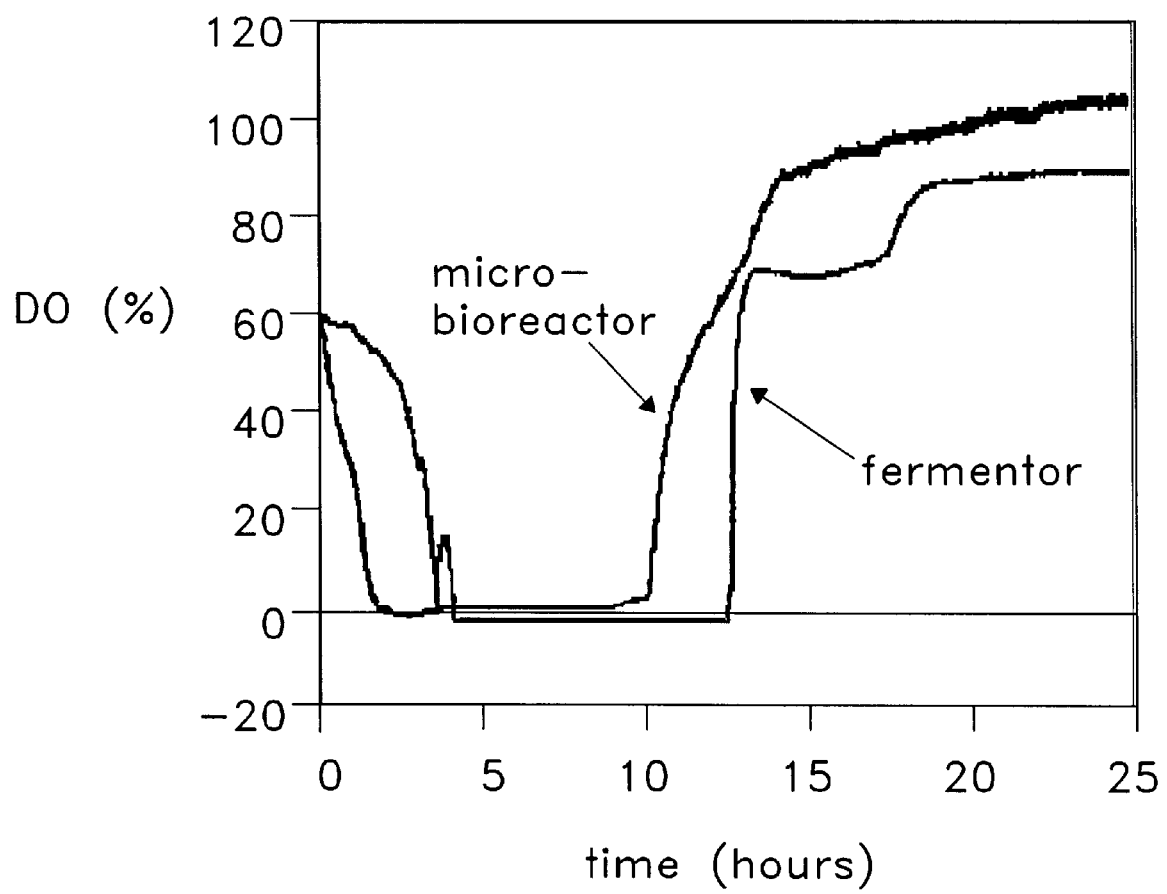
Figure 4C:
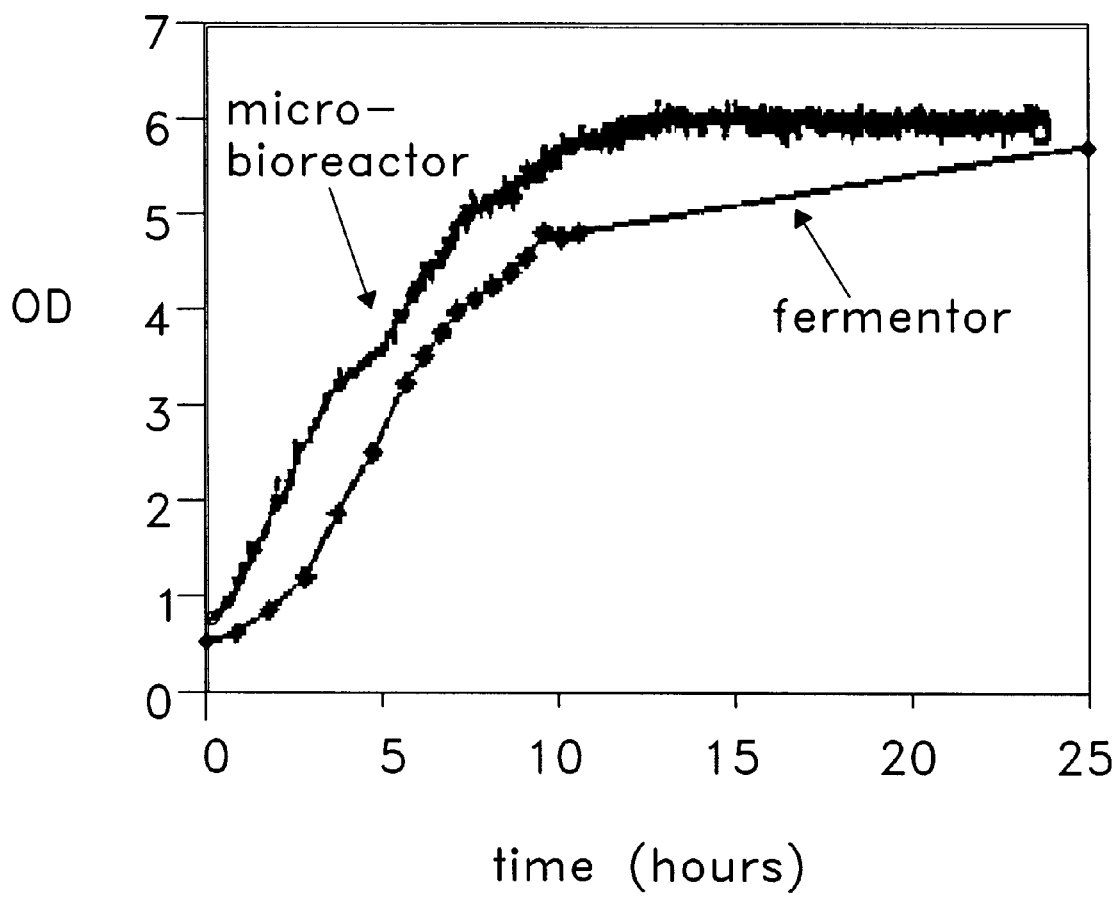

The performance of the microbioreactor was tested by conducting parallel fermentations of *E. coli* in the cuvette and a 1-liter BIOFLO™ III (New Brunswick Scientific Co., Inc.) fermentor. Both were inoculated at the same time from the same seed culture after setting them to run under identical $K_1$ as (the fermentor was run at 300 rpm and 1 vvm aeration (21 hr$^{-1}$)). The $K_1a$ was arbitrarily chosen as agitation/aeration above this level led to foaming in the microbioreactor which was clearly caused by the ad hoc fabrication of the aeration system and an inefficient magnetic stir-bar which served as the agitator. Comparisons of the resulting profiles are shown in FIGS. 4(a)–4(c).

As can be seen, the profiles of pH, DO and OD are very similar in both processes. The patterns of oxygen depletion during the exponential growth as well as the recovery of DO to 100% at the end of the process are similar in both cases. The correlation coefficient between the OD of the two fermentations was 0.984, indicating very similar growth profiles in the two cultures. However, all the specific points of the microbioreactor process occurred approximately 2 hours earlier. Additional investigation showed that after about 1 hour, the microbioreactor heated up approximately 3° C. above the ambient temperature due to Joule heating (the cuvette was not equipped for temperature control).

Thus, while the cells in the 1-liter bioreactor were cultivated at 25° C., the microbioreactor cells were cultivated at 28° C. Taking into account that the optimal temperature for *E. coli* is 37° C., the temperature elevation may explain the slightly increased cell growth rate and decreased lag time in the microbioreactor. One solution to the problem would be the use of a small thermoelectric device for temperature control.

To ensure that pH and OD measurements did not affect each other, their values were verified by offline measurements in the beginning and the end of the process. The results are shown in the respective figures (FIGS. 4(a) and 4(c)). Offline pH and OD values agreed very well with the online values and demonstrated stability over the period of operation, i.e., no drift.

This example demonstrates that a bioprocess can be successfully performed in small volumes (about 2 ml in this example). The use of semiconductor excitation sources and detectors in this design makes for a very compact and low-cost detection system.

The foregoing embodiments and advantages are merely exemplary and are not to be construed as limiting the present invention. The description of the present invention is intended to be illustrative and is not intended to limit the scope of the claims. Many alternatives, modifications and variations will be apparent to those skilled in the art. In the claims, means-plus-function clauses are intended to cover the structures described herein as performing the recited function and not only structural equivalents, but also equivalent structures.

The above cited references, including any and all articles are incorporated by reference herein where appropriate for appropriate teachings of additional or alternative details, features and/or technical background.

What is claimed is:

1. A method of measuring at least two cultivation parameters in a cell culture, comprising:
   (a) establishing at least one cell culture in at least one bioreactor, wherein each bioreactor comprises at least two optical chemical sensors;
   (b) exciting the at least two optical chemical sensors to generate emission and/or light absorption;
   (c) detecting the emission and/or absorption generated by the at least two optical chemical sensors in (b); and
   (d) analyzing the detected emission and/or absorption detected in (c) to assess the at least two cultivation parameters measured.

2. The method of claim 1, wherein the at least two optical chemical sensors are excited using at least one light emitting diode per optical chemical sensor.

3. The method of claim 1, wherein the emission and/or absorption is detected using at least one photodetector, wherein the wavelength range of the photodetector corresponds to an emission and/or absorption wavelength of the photodetector's respective optical chemical sensor.

4. The method of claim 1, wherein the at least two cultivation parameters measured are selected from the group consisting of: pH, dissolved oxygen, carbon dioxide, glucose concentration, nutrient concentration, lactate concentration, phosphate concentration, ammonia concentration, metal ion concentration, temperature and combinations thereof.

5. The method of claim 1, wherein an optical density of the cell culture is measured.

6. A method of measuring at least two cultivation parameters in at least two cell cultures, comprising:
   (a) establishing at least one cell culture in at least two bioreactors in parallel, wherein each bioreactor comprises at least two optical chemical sensors;

(b) exciting the optical chemical sensors to generate emission and/or light absorption;

(c) detecting the emission and/or absorption generated by the optical sensors in (b); and (d) analyzing the detected emission and/or absorption detected in (c) to assess the at least two cultivation parameters measured.

7. The method of claim 6, wherein the at least two optical chemical sensors are excited using at least one light emitting diode per optical chemical sensor.

8. The method of claim 6, wherein the emission and/or absorption is detected using a spectrometer and diode array.

9. The method of claim 6, wherein the at least two cultivation parameters measured are selected from the group consisting of: pH, dissolved oxygen, carbon dioxide, glucose concentration, phosphate concentration, ammonia concentration, lactate concentration, metal ion concentration, nutrient concentration, temperature and combinations thereof.

10. The method of claim 6, wherein the optical densities of the at least two cell cultures are measured.

11. A method of optimizing at least two cultivation parameters in a cell culture, comprising:

(a) establishing at least one cell culture in at least one bioreactor, wherein each bioreactor comprises at least two optical chemical sensors;

(b) exciting the at least two optical chemical sensors to generate emission and/or light absorption;

(c) detecting the emission and/or absorption generated by the at least two optical chemical sensors in (b); and (d) analyzing the detected emission and/or absorption in (c) to determine whether or not to adjust culture conditions to obtain optimization of the at least two cultivation parameters.

12. The method of claim 11, wherein the at least two optical chemical sensors are excited using at least one light emitting diode per optical chemical sensor.

13. The method of claim 11, wherein the emission and/or absorption is detected using at least one photodetector, wherein the wavelength range of the at least one photodetector corresponds to an emission and/or absorption wavelength of the photodetector's respective optical chemical sensor.

14. The method of claim 11, wherein the at least two cultivation parameters measured are selected from the group consisting of: pH, dissolved oxygen, carbon dioxide, glucose concentration, nutrient concentration, temperature, lactate concentration, ammonia concentration, phosphate concentration, metal ion concentration and combinations thereof.

15. The method of claim 11, wherein an optical density of the cell culture is determined.

16. A method of optimizing at least two cultivation parameters in at least two cell cultures, comprising:

(a) establishing at least one cell culture in at least two bioreactors in parallel, wherein each bioreactor comprises at least two optical chemical sensors;

(b) exciting the optical chemical sensors to generate emission and/or light absorption;

(c) detecting the emission and/or absorption generated by the optical chemical sensors; and (d) analyzing the detected emission and/or absorption obtained in (c) to determine whether or not to adjust culture conditions to obtain optimization of the at least two cultivation parameters.

17. The method of claim 16, wherein the optical chemical sensors are excited using at least one light emitting diode per optical chemical sensor.

18. The method of claim 16, wherein the emission and/or absorption is detected using a spectrometer and diode array.

19. The method of claim 16, wherein the two cultivation parameters measured are selected from the group consisting of: pH, dissolved oxygen, carbon dioxide, glucose concentration, nutrient concentration, temperature, lactate concentration, ammonia concentration, phosphate concentration, metal ion concentration and combinations thereof.

20. The method of claim 16, wherein an optical density of each of the at least two cell cultures is are determined.

* * * * *